US011253535B2

(12) United States Patent
Cancela et al.

(10) Patent No.: US 11,253,535 B2
(45) Date of Patent: Feb. 22, 2022

(54) CARBOLINE DERIVATIVES OR PHOSPHOROUS DERIVATIVES FOR THE TREATMENT OF MUSCULAR MYOPATHIES AND TRAUMATIC INJURIES TO MUSCLES

(71) Applicant: Centre National de la Recherche Scientifique (C.N.R.S), Paris (FR)

(72) Inventors: José-Manuel Cancela, Palaiseau (FR); Sabine De La Porte, Versailles (FR); Antoine De Zelicourt, Versailles (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/060,895

(22) PCT Filed: Dec. 9, 2016

(86) PCT No.: PCT/FR2016/053289
§ 371 (c)(1),
(2) Date: Jun. 8, 2018

(87) PCT Pub. No.: WO2017/098173
PCT Pub. Date: Jun. 15, 2017

(65) Prior Publication Data
US 2019/0022122 A1    Jan. 24, 2019

(30) Foreign Application Priority Data

Dec. 9, 2015  (FR) ..................... 15 62040

(51) Int. Cl.
| *A61K 31/7084* | (2006.01) |
| *A61K 31/496*  | (2006.01) |
| *A61K 31/706*  | (2006.01) |
| *A61K 31/7064* | (2006.01) |
| *A61K 31/7076* | (2006.01) |
| *A61P 21/00*   | (2006.01) |
| *A61K 31/708*  | (2006.01) |
| *A61K 31/137*  | (2006.01) |
| *A61K 31/4166* | (2006.01) |
| *A61K 31/55*   | (2006.01) |
| *A61K 31/573*  | (2006.01) |
| *A61K 31/58*   | (2006.01) |

(52) U.S. Cl.
CPC ........ *A61K 31/7084* (2013.01); *A61K 31/496* (2013.01); *A61K 31/706* (2013.01); *A61K 31/708* (2013.01); *A61K 31/7064* (2013.01); *A61K 31/7076* (2013.01); *A61P 21/00* (2018.01); *A61K 31/137* (2013.01); *A61K 31/4166* (2013.01); *A61K 31/55* (2013.01); *A61K 31/573* (2013.01); *A61K 31/58* (2013.01); *A61K 2300/00* (2013.01)

(58) Field of Classification Search
CPC .............. A61K 31/7084; A61K 31/708; A61K 31/706; A61K 31/496; A61K 31/7064; A61K 31/7076; A61K 31/58; A61K 31/55; A61K 31/4166; A61K 31/137; A61K 31/573; A61K 2300/00; A61P 21/00

See application file for complete search history.

(56) References Cited

U.S. PATENT DOCUMENTS

| 8,003,324 B2 * | 8/2011 | Dudley, Jr. ........ A61K 31/7084 435/6.17 |
| 8,133,872 B2 * | 3/2012 | Kim ................... A61K 31/7064 514/43 |
| 9,114,151 B2 * | 8/2015 | Dudley, Jr. .......... A61K 31/194 |
| 9,211,301 B2 * | 12/2015 | Dudley, Jr. ........ A61K 31/7084 |
| 2009/0306006 A1 | 12/2009 | Kim et al. |
| 2012/0308542 A1 | 12/2012 | Dudley, Jr. |

FOREIGN PATENT DOCUMENTS

| IT | FI20070077 A1 | 9/2008 |
| WO | WO 2009/101399 A1 | 8/2009 |
| WO | WO 2011/003018 A2 | 1/2011 |

OTHER PUBLICATIONS

Russo et al., "ACE Inhibition to Slow Progression of Myocardial Fibrosis in Muscular Dystrophies," Trends in Cardiovascular Medicine, 28, 330-337 (2018): copy supplied by applicant.*
Chemical Abstracts Database, Accession No. 2008:1345956, 2008 "Protective effect of nicotinamide adenine dinucleotide on Adriamycin-induced cardiomyopathy in rats".
Goody, M.F. et al. 2012 "NAD+ Biosynthesis Ameliorates a Zebrafish Model of Muscular Dystrophy" PLOS Biology 10: e1001409 (in 17 pages).
Jiang, et al. 2009 "Mechanism-based small molecule probes for labeling CD38 on live cells" *J. Am. Chem. Soc.* 131: 1658-1659.
Kwong, et al. 2012 "Catalysis-based inhibitors of the calcium signaling function of CD38" *Biochemistry* 51: 555-564.
Lopez, et al. 2005 "Altered $Ca^{2+}$ homeostasis in human uremic skeletal muscle: Possible involvement of cADPR in elevation of intracellular resting $[Ca^{2+}]$" *Nephron Physio* 100: 51-60.
Ruegg 2013 "Pharmacological prospects in the treatment of Duchenne muscular dystrophy" *Current Opinion in Neurology* 26(5): 577-584.
Davidson, S.M. et al. 2015 "Inhibition of NAADP signalling on reperfusion protects the heart by preventing lethal calcium oscillations via two-pore channel 1 and opening of the mitochondrial permeability transition pore" Cardiovascular Research 108: 357-366.
Gissel, H. 2005 "The Role of $Ca^{2+}$ in Muscle Cell Damage" Ann. N.Y. Acad. Sci. 1066: 166-180.

(Continued)

*Primary Examiner* — Lawrence E Crane
(74) *Attorney, Agent, or Firm* — Knobbe, Martens, Olson & Bear, LLP

(57) ABSTRACT

A method of treating Duchenne muscular dystrophy (DMD), Becker muscular dystrophy (BMD), a cardiomyopathy or a muscular traumatism in a subject includes administering to the subject certain ADP ribosylcyclase antagonist compounds, certain cyclic ADP ribose (cADPR) antagonist compounds, certain nicotinic acid adenine dinucleotide phosphate (NAADP) antagonist compounds or a mixture of these compounds.

14 Claims, 18 Drawing Sheets

(56) References Cited

OTHER PUBLICATIONS

Kwong, A.K.Y. et al. 2012 "Catalysis-Based Inhibitors of the Calcium Signaling Function of CD38" Biochemistry 51: 555-564.

Mayo Clinic "Angiotensin-converting enzyme (ACE) inhibitors" (on the World-Wide Web at: mayoclinic.org/diseases-conditions/high-blood-pressure/in-depth/ace-inhibitors/art-20047480, downloaded Sep. 14, 2020).

Rosen, D. et al. 2009 "Analogues of the Nicotinic Acid Adenine Dinucleotide Phosphate (NAADP) Antagonist Ned-19 Indicate Two Binding Sites on the NAADP Receptor" The Journal of Biological Chemistry vol. 284, No. 50, pp. 34930-34934.

Sethi, J.K. et al. 1997 "7-Deaza-8-bromo-cyclic ADP-ribose, the First Membrane-permeant, Hydrolysis-resistant Cyclic ADP-ribose Antagonist" The Journal of Biological Chemistry vol. 272, No. 26, Issue of Jun. 27, pp. 16358-16363.

Walseth, T.F. and Lee, H.C. 1993 "Synthesis and characterization of antagonists of cyclic-ADP-ribose-induced $Ca^{2+}$ release" Biochimica et Biophysica Acta 1178: 235-242.

\* cited by examiner

B

Diaphragm mdx  mdx/CD38-/-  CD38-/-

C

D

B

C

A

B

D

NED-19 (NAADP antagonist)

A

$R_1 = C_4H_9$
$R_2 = OH$
$R_3 = F$
$R_4 = CONH_2$

CZ-27 (CD38 antagonist)

B $R_1$ = Br
$R_2$ = N
$R_3$ = OH
$R_4$ = OH
$R_5$ = OH

8-Bromo-cADP-ribose (cADP-ribose antagonist)

A

B

C

D

E

CARBOLINE DERIVATIVES OR PHOSPHOROUS DERIVATIVES FOR THE TREATMENT OF MUSCULAR MYOPATHIES AND TRAUMATIC INJURIES TO MUSCLES

CROSS-REFERENCE TO RELATED APPLICATIONS

This application is U.S. National Phase of International Application PCT/FR2016/053289, filed Dec. 9, 2016 designating the U.S., and published in English as WO 2017/098173 A2 on Jun. 15, 2017, which claims priority to French Patent Application No. 15 62040 filed Dec. 9, 2015.

FIELD

The present invention relates to the field of medicine. It relates more particularly to the use of compounds for preventing and/or treating, in a subject, myopathy, typically muscular dystrophy or cardiomyopathy, or muscle trauma. The invention also relates to compositions, in particular pharmaceutical compositions comprising such compounds, and corresponding kits, as well as their uses for preventing and/or treating muscular myopathy or trauma. The compounds and compositions according to the invention may typically be advantageously used to prevent and/or treat muscular dystrophy, cardiomyopathy or muscular trauma, preferably Duchenne Muscular Dystrophy (DMD), Becker Muscular Dystrophy (BMD) and/or or a symptom or abnormality characteristic of DMD or BMD.

BACKGROUND

Muscular dystrophies are a group of diseases characterized by weakness and progressive degeneration of the body's muscles and inflammation. They atrophy little by little, i.e. they lose their strength and volume. These are genetic diseases that may begin at birth, during childhood or in adulthood. About forty different genes are involved in muscular dystrophies. It is difficult to know the frequency of all dystrophies, but some studies estimate that about 1 in 3,500 people have DMD. Dystrophies may affect anyone and appear at any age. There are more than 30 forms, which differ by the age of onset, the muscles affected, and the severity. These are diseases that progressively worsen and for which there is no treatment. The muscles affected in the event of muscular dystrophy are mainly those that allow voluntary movements, especially the muscles of the legs and arms. The respiratory muscles and the heart may sometimes be affected. This is the case in DMD. Unfortunately, most people with muscular dystrophy gradually lose the ability to walk. Other symptoms may include muscle weakness, including heart, gastrointestinal, eye, and inflammatory disorders.

Usually two major groups of muscular dystrophies are differentiated:
  congenital muscular dystrophies (CMD), which begin in the first 6 months of life. There are about 10 forms of variable severity, including CMD with primary merosin deficiency (a constituent of the muscle cell membrane), Ullrich's CMD, rigid spine syndrome, and Walker-Warburg's syndrome; and
  muscular dystrophies beginning later in childhood or adulthood such as Duchenne muscular dystrophy (DMD); Becker muscular dystrophy (BMD); Emery-Dreyfuss muscular dystrophy (there are several forms); fascio-scapulo-humeral muscular dystrophy, also called Landouzy-Dejerine myopathy; limb girdle muscular myopathies, so called because they affect, in particular, the muscles around the shoulders and hips; myotonic dystrophies (types I and II), which include Steinert's dystrophy that is characterized by myotonia (i.e. the muscles fail to relax normally after contraction); and oculopharyngeal muscular dystrophy.

The best known and most common type of muscular dystrophy is Duchenne muscular dystrophy (DMD), also known as Duchenne muscular myopathy. It originates from the loss of function of a gene carried by the X chromosome in the p21 region coding for dystrophin, a protein located under the membrane and playing a role in the contraction of the muscle. DMD is a fairly common disease in the world, affecting only the male sex. Its incidence is one in 3,500. At birth, no symptoms are observed, but during development, there is a gradual loss of motility. The disease manifests itself by a progressive degeneration of the skeletal, smooth and cardiac muscles as well as by cognitive and behavioral deficits. This degeneration is partly related to an excessive increase of calcium which leads to the activation of proteases at the origin of cell death. At the age of 12, these children lose the ability to walk and more than half do not live beyond 20-30 years old. The causes of death are either muscular respiratory failure or cardiomyopathy. There is no effective treatment against DMD today.

The symptoms of Becker muscular dystrophy are comparable to those of Duchenne muscular dystrophy, but they are less marked and the evolution is less rapid. Symptoms begin around 5 to 15 years of age, sometimes later, and are characterized by a progressive loss of muscle strength in the limbs and trunk. In more than half of the cases, walking remains possible until the age of about 40 years of age. On the other hand, a heart attack is frequent and may appear from the beginning.

Currently the only treatments used against myopathies, especially against muscular dystrophies, aim to reduce inflammation and progression of the disease using glucocorticoids (prednisone and prednisolone). These treatments have modest beneficial effects but may cause many side effects that may lead to complications, especially in the case of long-term treatments. Side effects include weight gain that may compromise mobility, reduced bone mineral density with increased risk of fractures, cataract development, and increased intraocular pressure. β-blockers, phosphodiesterase inhibitors, and angiotensin-converting enzyme inhibitors are specifically used to improve the cardiac function, in particular to reduce the development of cardiac hypertrophy and arrhythmia observed in the patient. However, these treatments have no effect on cardiac or skeletal muscle degeneration. Moreover, they are used later for healing purposes in order to reduce the symptoms that have appeared, but can not be used in a preventive manner.

The inventors now describe molecules or compounds, and compositions comprising such molecules or compounds, wherein the compounds, active throughout the musculature (skeletal, cardiac and smooth muscles), are able not only to treat a diagnosed myopathy, or muscle trauma, but also to prevent the occurrence of myopathy. In particular, these compounds are capable of reducing the necrotic disorders observed in the heart, diaphragm and skeletal muscles of subjects suffering from DMD and BMD, and of preventing such damage in subjects at risk of developing myopathy, typically muscular dystrophy.

SUMMARY

The invention relates to molecules (also referred to herein as "compounds") for the prevention or treatment of myopathies, typically muscular dystrophies and cardiomyopathies, and muscular trauma. In the context of the present invention, the terms "myopathy" or "myopathies" do not designate and do not cover uremic myopathy.

The molecules of the invention are preferably for the prevention or treatment of Duchenne muscular dystrophy (DMD) or Becker muscular dystrophy (BMD) or a symptom or abnormality characteristic of DMD or BMD.

In a preferred embodiment of the invention, the compound according to the invention: i) reduces or inhibits the activity of calcium channels and reduces the functional impairments of skeletal, smooth and/or cardiac muscle cells, ii) reduces muscle necrosis possibly present in skeletal, smooth and/or cardiac muscle cells and preferably, iii) reduces muscular inflammation.

A particular compound according to the invention for use in preventing or treating myopathy in a subject is an ADP ribosylcyclase antagonist compound (CD38 being an example of ADP ribosylcyclase), a cyclic ADP ribose antagonist compound ("cADPR" or "ADPRc"). and/or a nicotinic acid adenine dinucleotide phosphate antagonist compound ("NAADP" or "nicotinic acid adenine dinucleotide phosphate").

The invention furthermore relates to a compound or a mixture of compounds as described herein for use in treating muscular trauma or for preventing or treating myopathy in a subject, typically muscular dystrophy and/or cardiomyopathy, or at least one symptom, or at least one characteristic anomaly of the preferably several characteristic symptoms or anomalies (for example 2, 3, 4 or 5).

The invention furthermore relates to a composition, in the form of a pharmaceutical composition, comprising at least one compound according to the invention and a pharmaceutically acceptable carrier. One particular object typically relates to a pharmaceutical composition comprising, in addition to the at least one compound according to the invention, at least one other compound (different from the compounds according to the invention) that is therapeutically active (and recognized as such by those skilled in the art).

The invention also relates to the use of such a composition for preventing or treating myopathy or for treating muscular trauma in a subject. It also relates to the use of such a composition for treating muscular trauma or for preventing or treating muscular dystrophy or cardiomyopathy in a subject, typically at least one symptom or one anomaly that is characteristic of muscular dystrophy, preferably several symptoms (for example 2, 3, 4 or 5); preferably to prevent or treat DMD or BMD. The described uses may also be advantageously implemented in combination with at least one other therapeutically active compound (recognized as such by those skilled in the art and different from the compounds according to the invention), in particular in the treatment of muscular dystrophies or cardiomyopathies, typically at least one characteristic symptom or anomaly of DMD and/or BMD.

Finally, the invention relates to a prophylactic or therapeutic kit comprising a compound (or a mixture of at least two, for example three, compounds according to the invention), and/or a composition according to the invention, and at least one other therapeutically active compound (recognized as such by those skilled in the art and different from the compounds according to the invention), in particular in the treatment of muscular dystrophies, typically at least one characteristic symptom or anomaly of the DMD and/or BMD, cardiomyopathy or muscular trauma, wherein the compounds are preferably in separate containers.

ADP-ribosylcyclase CD38 is an ectoenzyme that produces both cyclicADP-ribose (cADPR) and nicotinic acid adenine dinucleotide phosphate (NAADP). The cADPR activates the ryanodine receptors (RYRs) located in the sarcoplasmic reticulum (SR). The NAADP activates, via an intermediate protein, a calcium channel located at the level of the lysosome membrane called the "two-pore channel" (TPC) but also directly or indirectly recruits the RyRs.

The transient receptor potential cation channel 1 (TRPML1), a member of the mucolipin subfamily, may be indirectly recruited by NAADP. The CICR (calcium-induced calcium release) refers to a biological mechanism in which calcium ions induce the release of calcium ions contained in the SR. GPCR: G proteins/coupled receptors EC: extracellular compartment, IC: intracellular compartment.

Figure 2:
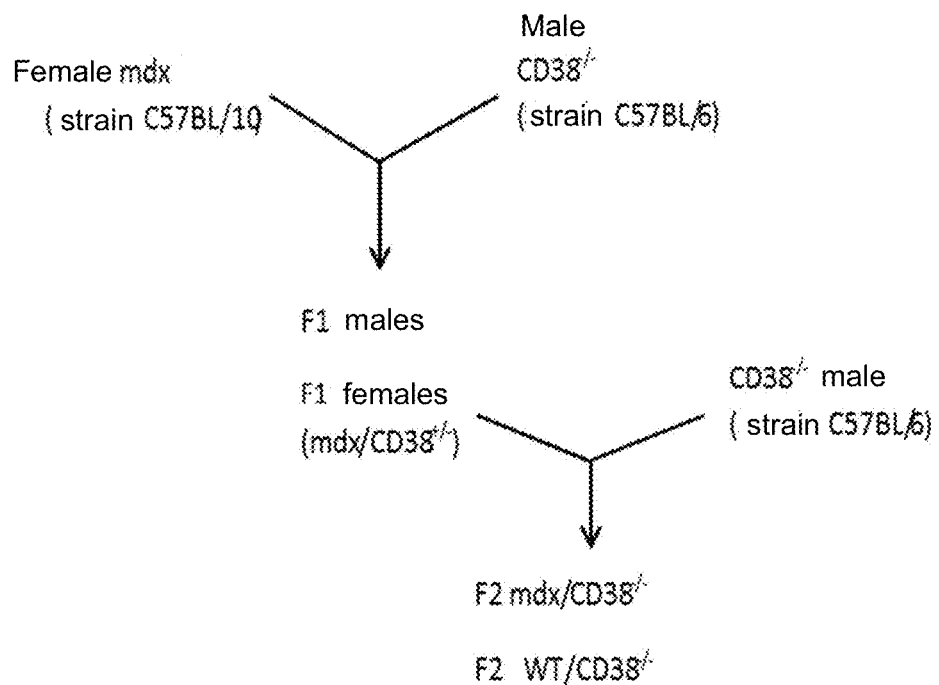

FIG. 2: Representation of crosses to obtain mdx/CD38$^{-/-}$ mice.

Figure 3:
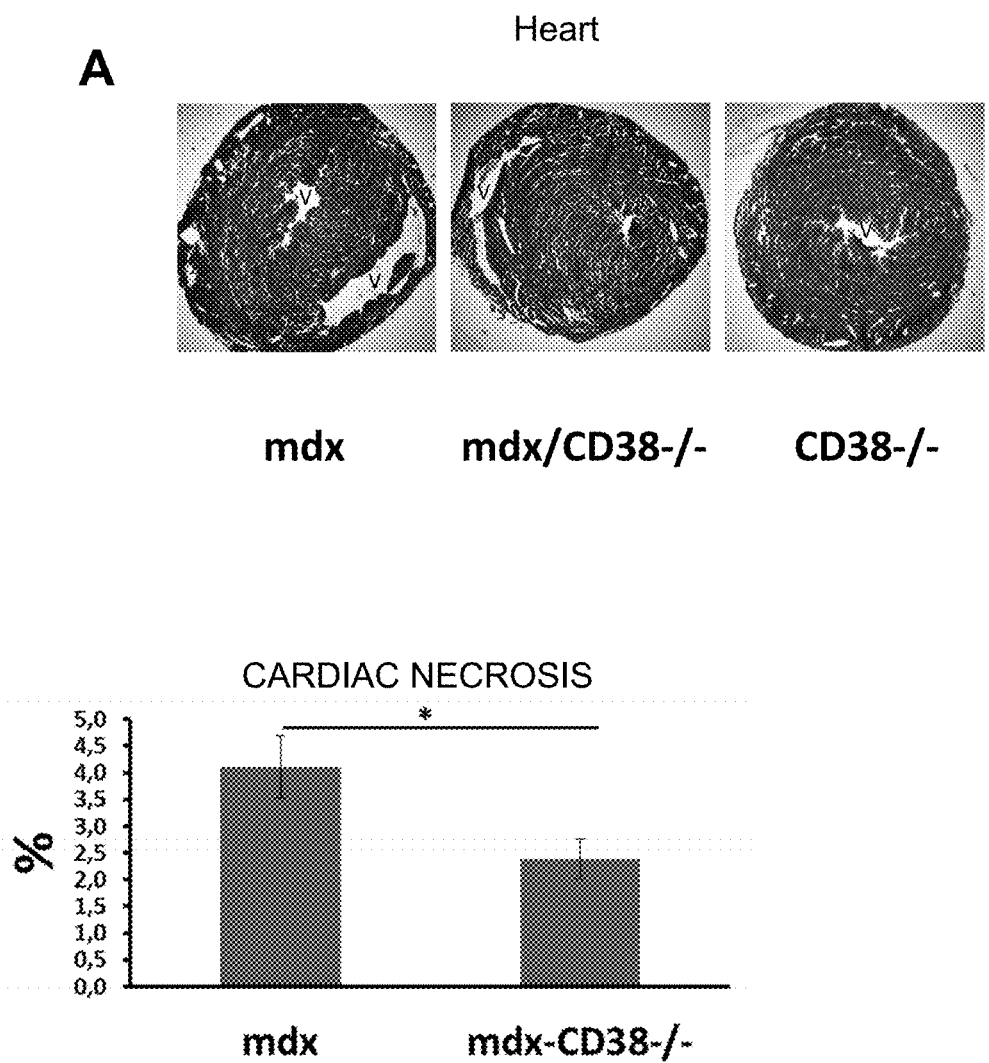
Figure 3:
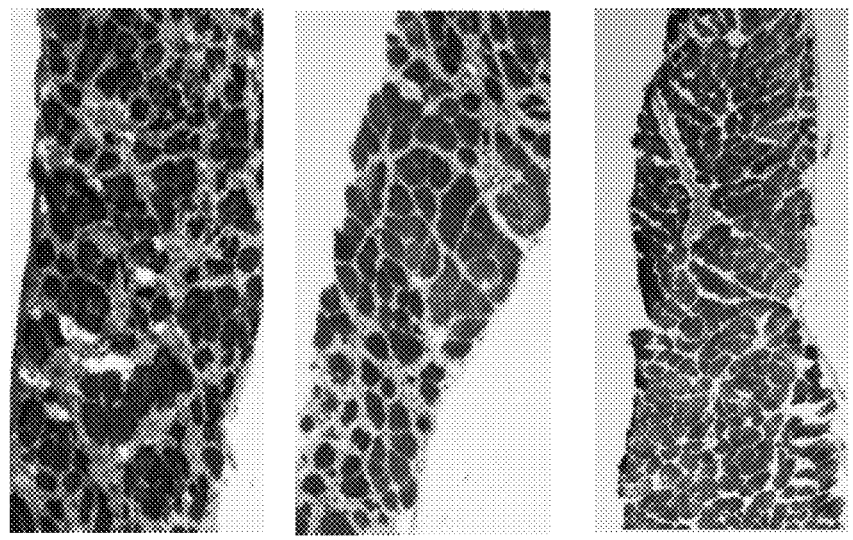
Figure 3:
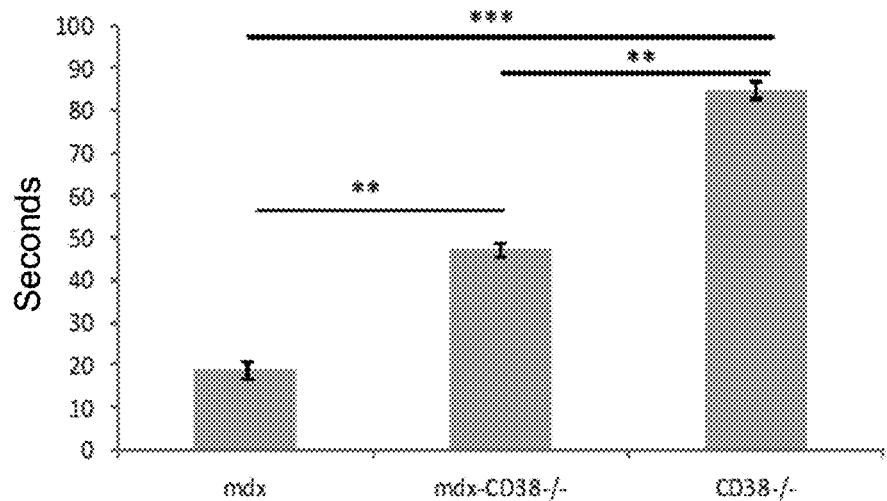
Figure 3:
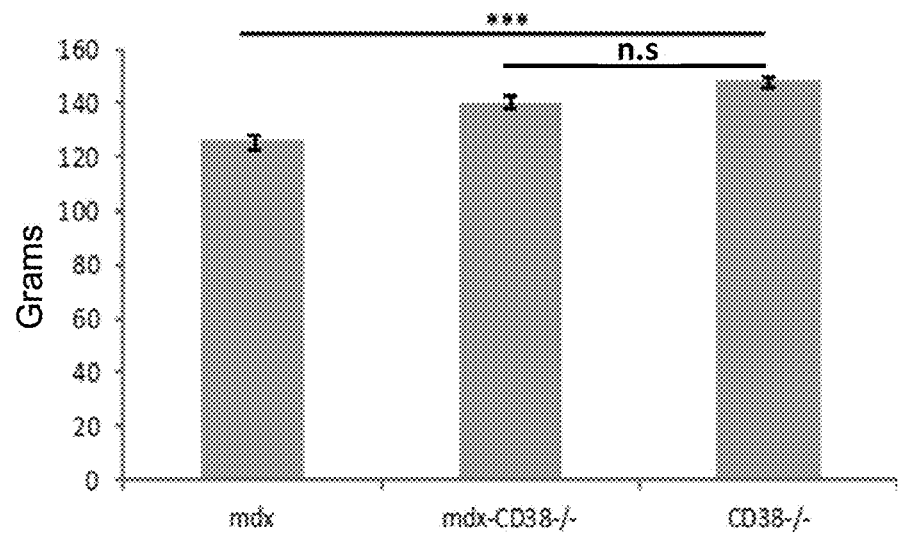
Figure 3:
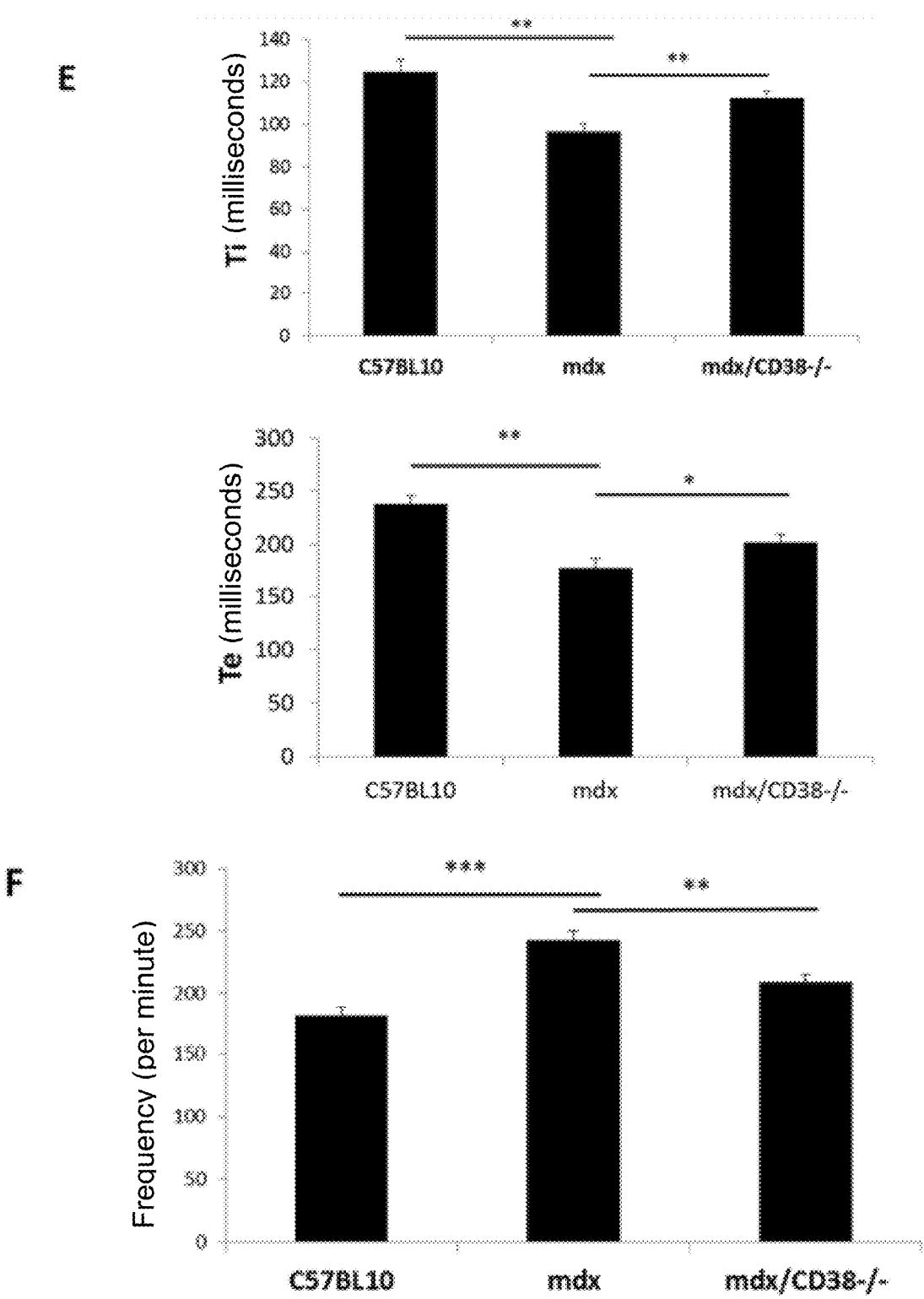

FIG. 3: (A-B) Structural benefit of disabling the CD38 gene in the mdx mouse. Improved heart and diaphragm structure in mdx mice invalidated for the CD38 gene. Reduction of necrosis in the heart (A) and diaphragm (B) in mdx/CD38$^{-/-}$ mice (n=7) was observed after Masson trichrome staining, compared with necrosis seen in mdx mice (n=13). The absence of CD38 reduced the infiltration of collagen into the tissues. The percentage of necrosis area in the heart (Masson trichome stain) (A). A 50% reduction observed in mdx/CD38$^{-/-}$ mice (n=7) compared to mdx mice (n=13). The error bar represents ±SEM with a threshold of significance at *P≤0.05 (t-test). (C-F) Functional benefit of disabling the CD38 gene in the mdx mouse. (C) Fatigue resistance test on an inverted grid: the latency corresponds to the time taken by the mouse to release the grid. The longer the time, the greater the fatigue resistance. This time is reduced by 78% in the mdx mouse (n=27) compared to the CD38$^{-/-}$ mouse (n=45). Invalidation of the C38 gene in mdx mice (mdx/CD38$^{-/-}$, n=33) enhances the performance of the remaining mdx mice twice as long as the grid. (D) Measurement of force by the gripping test: The gripping force is reduced by 15% compared to CD38$^{-/-}$ mice (n=45). Invalidation of the CD38 gene in the mdx mouse (mdx/CD38$^{-/-}$, n=33) improves the gripping force, the reduction being only 5% compared to the CD38$^{-/-}$ mouse. The error bar represents ±SEM with a threshold of significance at *P≤0.05 (t-test) (n.s.=not significant). (E, F) Measurement of ventilatory mechanics by barometric plethysmography: (E) inspiratory and expiratory times (Ti (top) and Te (bottom)) are reduced by about 25% in mdx mice, and (F) the respiratory rate is increased by 10%. These variations correspond to adaptations to compensate for muscle failure. Invalidation of the CD38 gene in the mdx mouse (mdx/CD38$^{-/-}$, n=9) improves these parameters. The error bar represents ±SEM with a significance threshold at *P≤0.05 (t-test and Mann-Whitney).

Figure 4:
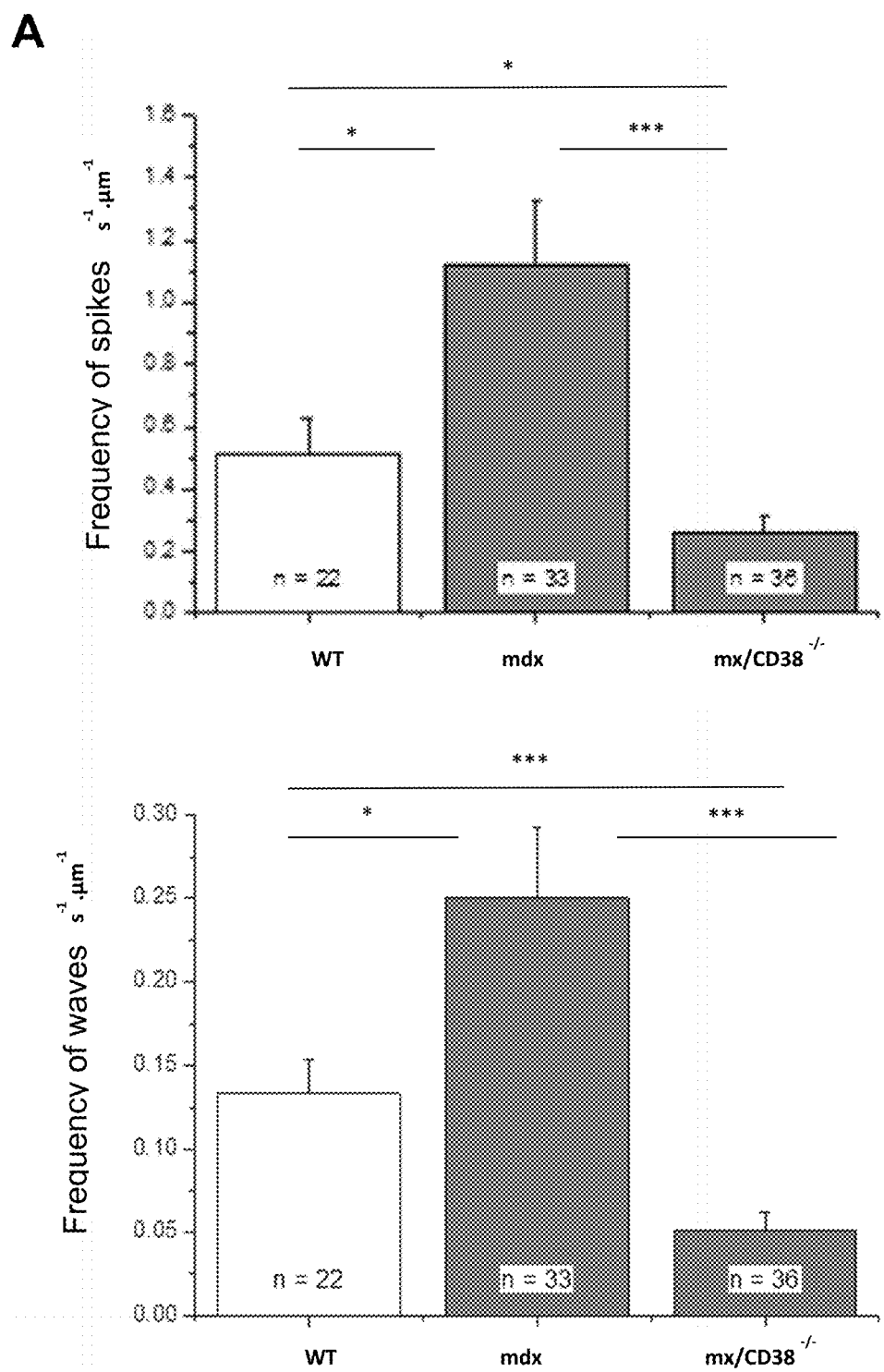
Figure 4:
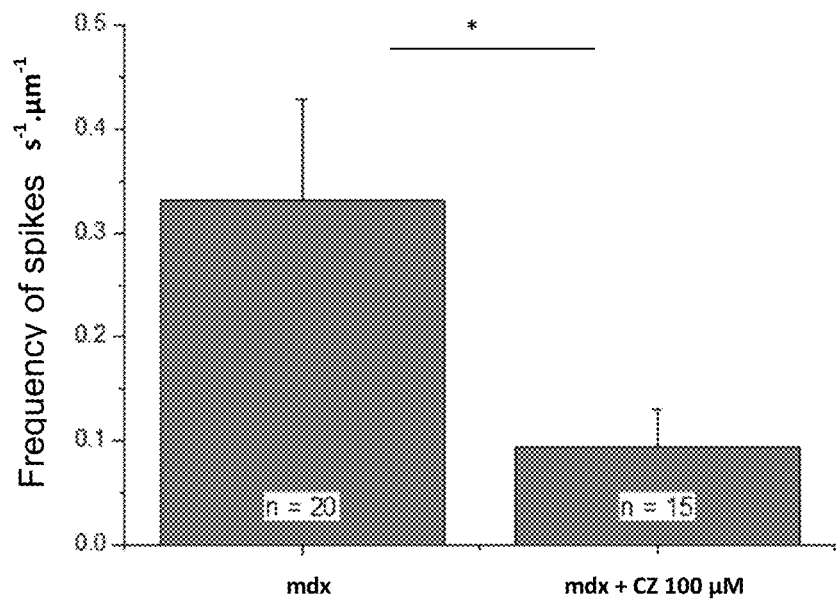
Figure 4:
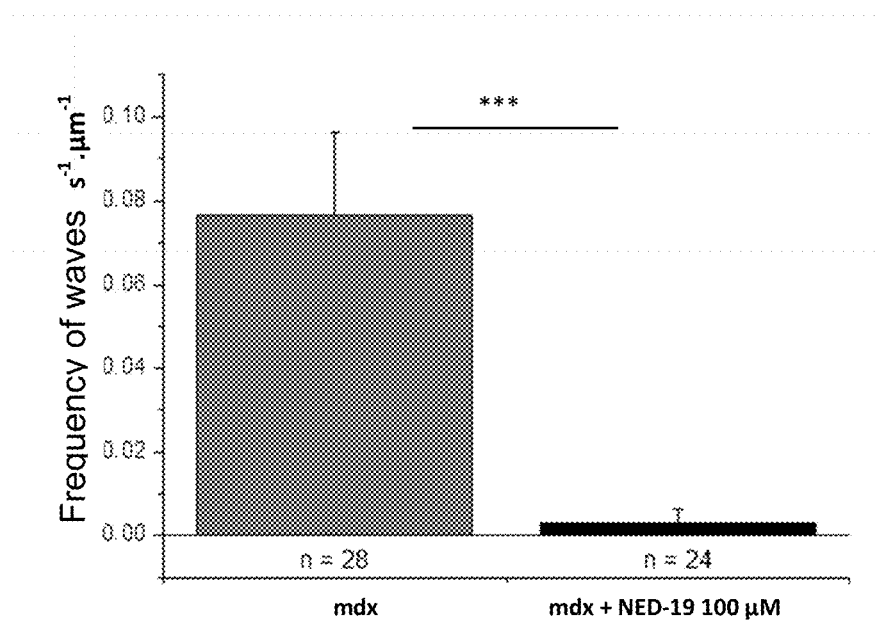

FIG. 4: Frequency of spontaneous spikes and calcium waves in WT, mdx and mdx/CD38$^{-/-}$ mouse cardiomyocytes. 1-way-ANOVA test with a Bonferroni correction. Significance level set at 0.05, with a *P<0.05; P<0.01, *P<0.001. (A) The spontaneous calcium activity of cardiomyocytes (calcium spikes and waves) of the mdx/CD38$^{-/-}$ mouse is reduced by 80% compared to the values of mdx mice. (B) The application of the CD38 CZ-27 antagonist to mdx mouse cardiomyocytes reduces the frequency of spikes by about 70%. (C) The application of NED-19, an NAADP antagonist, induces a significant reduction (about 90%) in spontaneous calcium wave activity.

Figure 5:
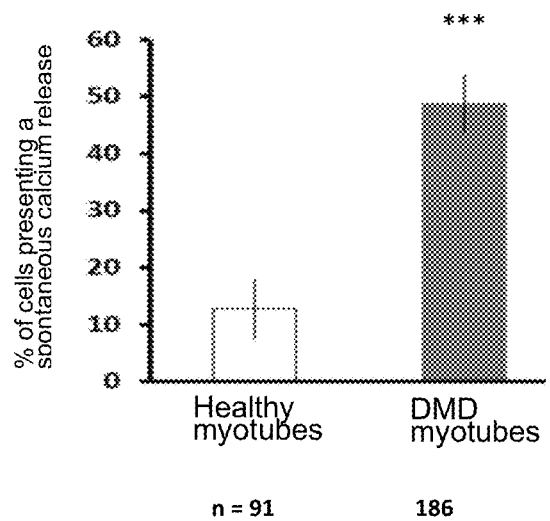
Figure 5:
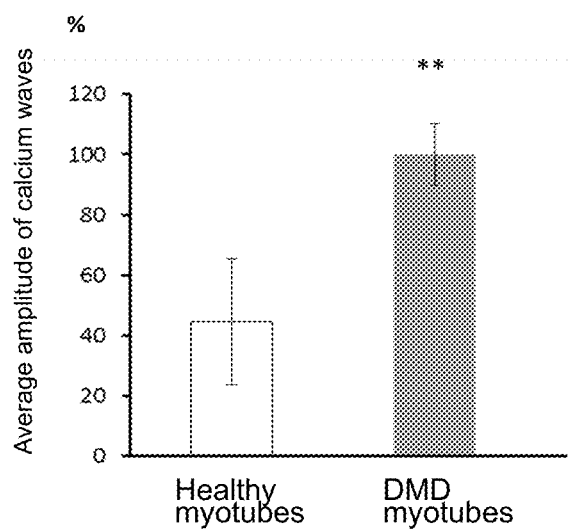
Figure 5:
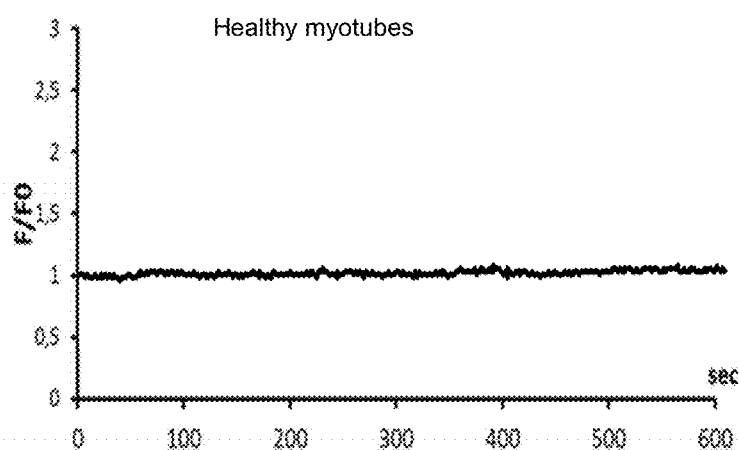
Figure 5:
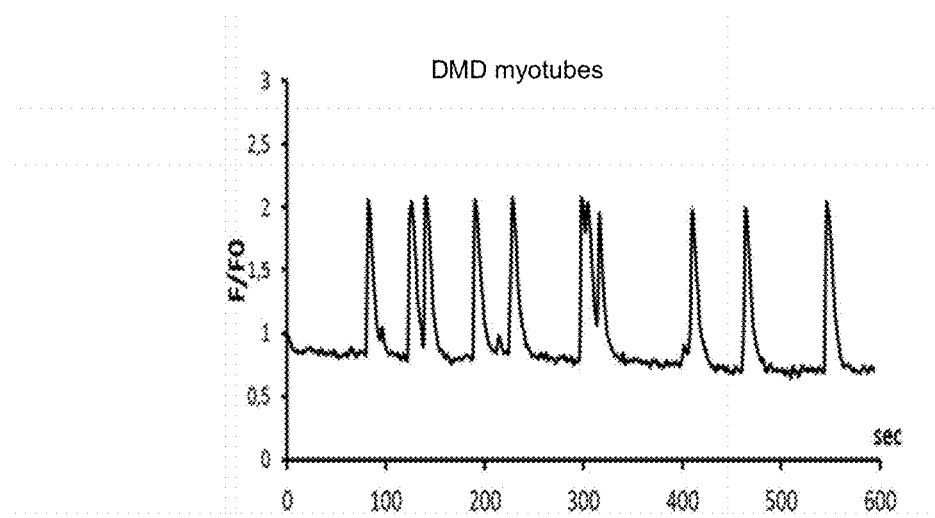
Figure 5:
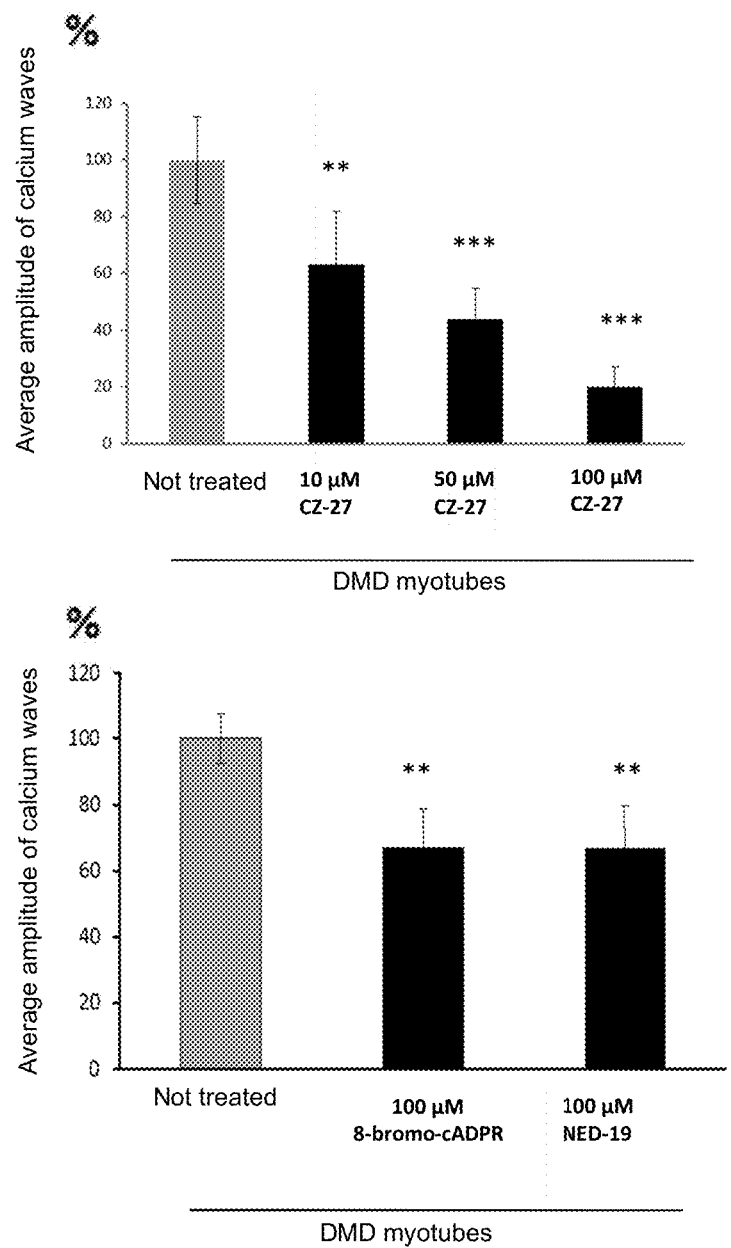
Figure 5:
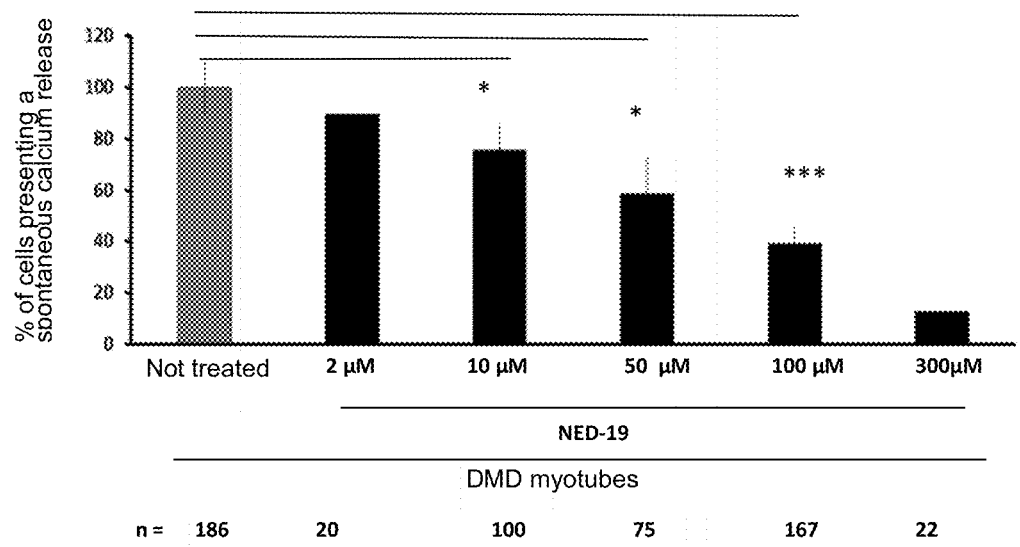

FIG. 5: Characteristics of spontaneous calcium activities (calcium waves) in DMD myotubes in the absence or in the presence of modulators of the CD38 enzyme pathway.

(A) Characterization of spontaneous calcium waves in DMD myotubes. Healthy myotubes mostly show low activity (13% of myotubes), while 49% of untreated DMD myotubes show significant spontaneous calcium activity. The amplitude of calcium oscillations in untreated DMD myotubes is increased by 60% compared with healthy myotubes. (B) Examples of trace recordings of a representative region of interest in myotubes and DMDs. (C) Amplitude of spontaneous calcium oscillations in DMD myotube cultures in the presence of modulators of the CD38 enzyme pathway. CZ-27 (CD38 antagonist) strongly reduces the amplitude of calcium oscillations in DMD myotubes (n=23). Similarly, 8-Bromo-cADPR (cADPR antagonist, 100 µM, n=48) and NED-19 (NAADP antagonist, 100 µM, n=167) reduce by 40% the amplitude of calcium oscillations in DMD myotubes. (D) The percentage of cells with spontaneous calcium activity is strongly reduced dose-dependently in the presence of NED-19 (2-300 µM). The t-test was used with a significance level set at 0.05, with a *P<0.05; P<0.01, *P<0.001, n=cell number.

Figure 6:
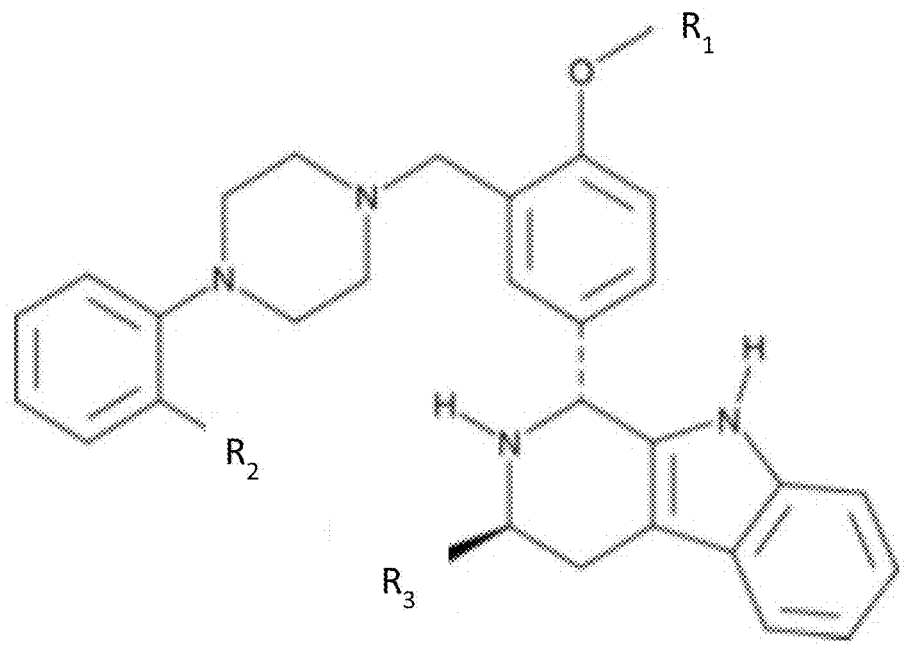

FIG. 6: NED-19 is an antagonist of NAADP [Rosen et al., J. Biol. Chem. (2009) 284, 34930-34934; Davidson et al. Cardiovascular Research (2015) 108, 357-366].

Figure 7:
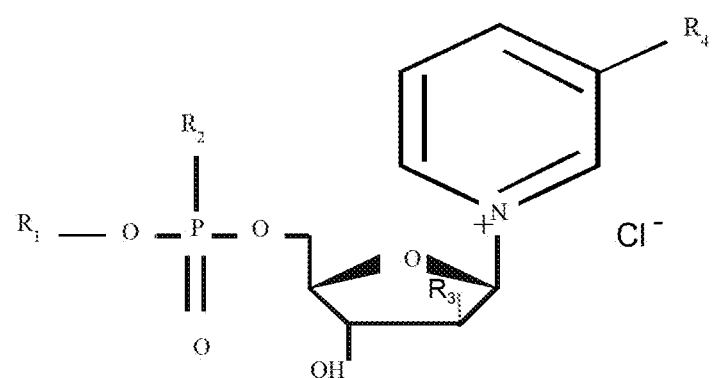
Figure 7:
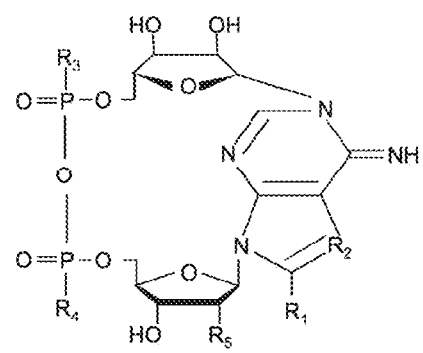

FIG. 7: Representation (A) of CZ-27 (CD38 antagonist) (Kwong et al., Biochemistry 2012, 51, 555-564) and (B) of 8-Bromo-cADP-ribose (cADP-ribose antagonist) (Walseth & Lee, Biochim. Biophys. Acta, 1178, 235-242 (1993).

Figure 8:
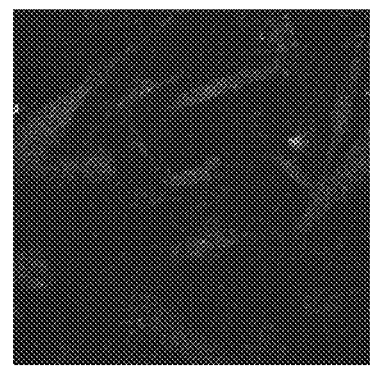
Figure 8:
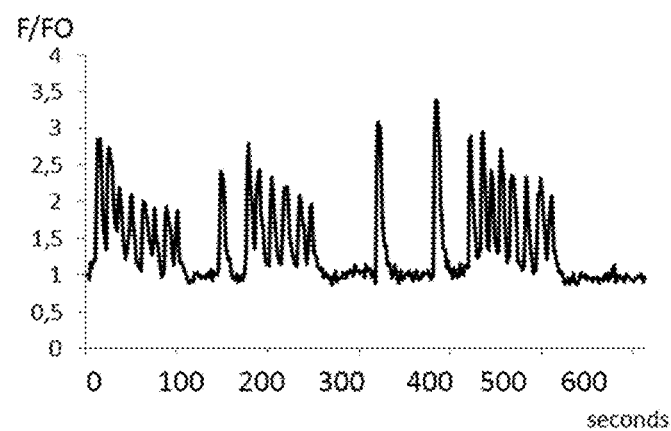
Figure 8:
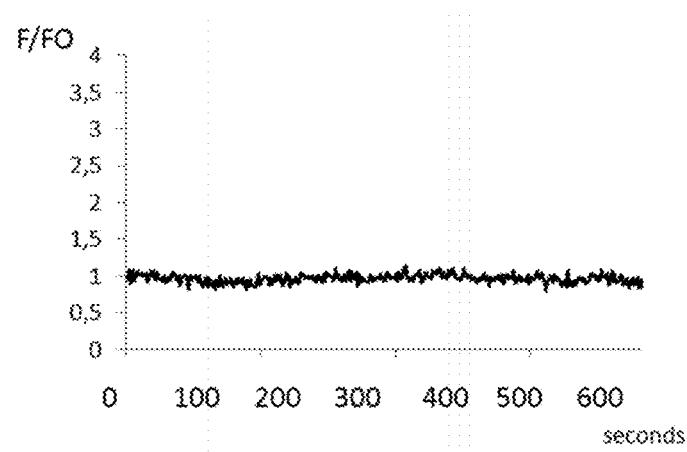
Figure 8:
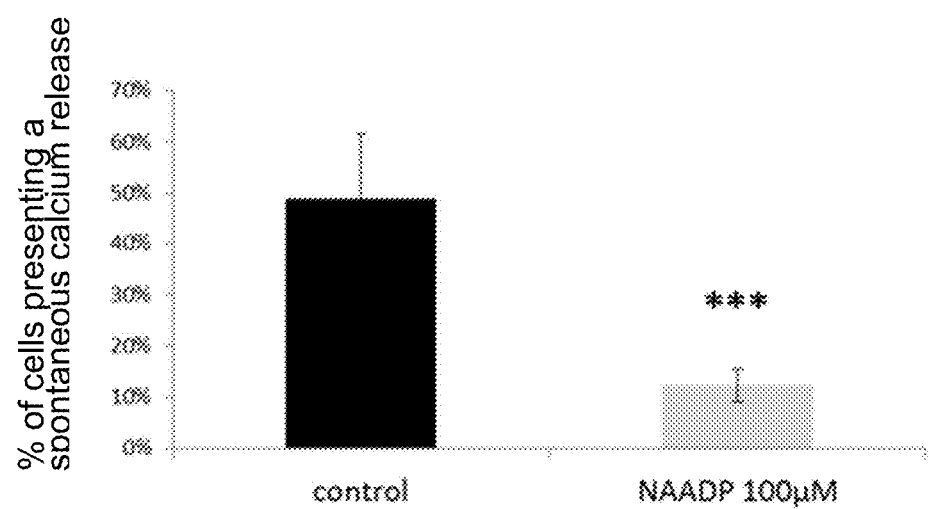
Figure 8:
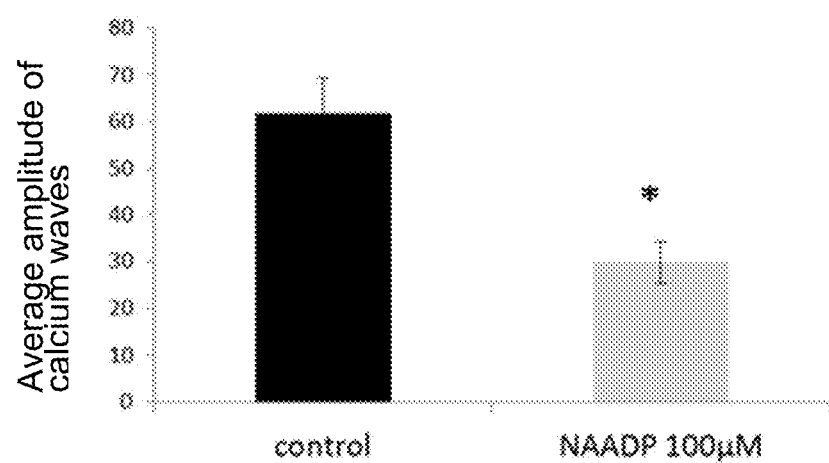

FIG. 8: Characteristics of spontaneous calcium activities (calcium waves) in DMD myotubes in the absence or in the presence of NAADP, modulator of the CD38 enzyme pathway.

(A) DMD myotubes loaded with a calcium probe (Fluo 4). Examples of trace recordings of a representative region of interest in control DMD myotubes (B) and treated for 30 min with NAADP (100 µM) (C). (D) the percentage of cells exhibiting spontaneous calcium activity is greatly reduced in the presence of 100 µM NAADP. (E) the amplitude of the spontaneous calcium oscillations is strongly reduced in the presence of 100 µM NAADP. The chi square (proportion of active cells) and t-test (mean peak amplitude) were used with a significance level set at 0.05, with a *P<0.05 ***P<0.001.

DETAILED DESCRIPTION

Figure 1:
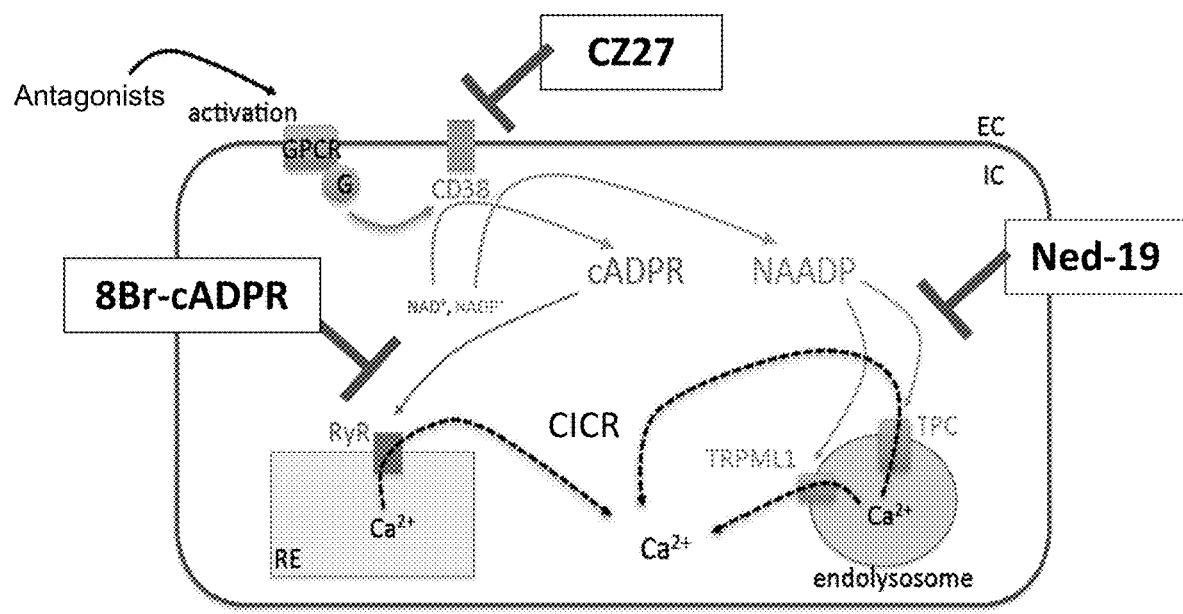
FIG. 1: Schematic representation of the CD38 signaling pathway.

The inventors have demonstrated that CD38, and its metabolites (see FIG. 1) including NAADP, are key therapeutic targets in the treatment of muscular myopathies and traumas, and that the inhibition of the CD38 pathway makes it possible, in particular, to prevent or treat necrotic involvement of the heart and diaphragm as well as functional impairment of skeletal muscle.

To demonstrate this, the inventors developed an mdx/CD38$^{-/-}$ double mutant mice model (model of mice suffering from Duchenne myopathy and deficient in CD38), and then carried out a pharmacological study which made it possible to identify compounds capable of reducing or inhibiting the calcium channel activity of muscle cells and restoring cellular functionality comparable to that encountered under non-pathological conditions. The effectiveness of the compounds preselected by the inventors has been tested and demonstrated by these same inventors on the cardiomyocytes of a mammal (i.e. on cardiomyocytes of the mouse model) as well as on a line of human muscle cells (myotubes) originating from a patient with DMD. The compounds NED-19, 8-Bromo-cADPR, CZ-27 (see FIG. 6, 7) and their functional derivatives have thus been identified as compounds that may be used directly in the prevention and treatment of myopathies in that they are able to normalize the key parameters of muscle calcium homeostasis, reduce, preferably suppress, muscle necrosis and inflammation, and restore the functionality of skeletal muscle, and cardiac and diaphragm muscle.

The invention thus relates to an ADP ribosylcyclase (e.g. CD38) antagonist compound, a cyclic ADP ribose antagonist compound (cADPR), and/or a nicotinic acid adenine dinucleotide phosphate (NAADP) antagonist compound (identified in the present text as "compounds of interest"), and/or to a mixture of at least two of the compounds of interest or their functional derivatives, for example three, for use in preventing or treating myopathy, or treating muscular trauma, in a subject.

Examples of preferred compounds of interest according to the invention: i) reduce or inhibit the calcium channel activity of skeletal, smooth and/or cardiac muscle cells, ii) reduce muscular necrosis possibly present in skeletal, smooth and/or or cardiac muscle cells, and preferably iii) reduce muscle inflammation, wherein they are selected from NED-19, 8-Bromo-cADPR, CZ-27, a functional derivative thereof and a mixture thereof, preferably NED-19, 8-Bromo-cADPR, CZ-27 and a mixture thereof, for example the mixture of NED-19 and 8-Bromo-cADPR or the mixture of NED-19, 8-Bromo-cADPR and CZ-27. The functional derivatives of these compounds, in particular the functional derivatives of NED-19, 8-Bromo-cADPR, and CZ-27 are also capable of performing the functions i), ii) and preferably iii) described above and may be considered as additional preferred examples.

Furthermore, the invention relates to a compound or mixture of compounds as described herein for use in treating muscular trauma, or for preventing or treating myopathy in a subject, typically a muscular dystrophy and/or cardiomyopathy, or least one characteristic symptom or anomaly thereof, preferably several symptoms or anomalies characteristic thereof (e.g. 2, 3, 4 or 5).

A particular compound according to the invention that is usable in a prevention or treatment method as described in the present text is an antagonist compound of ADP ribosylcyclases, typically CD38.

A preferred CD38 antagonist compound is preferably selected from a nicotinamide compound of formula (I):

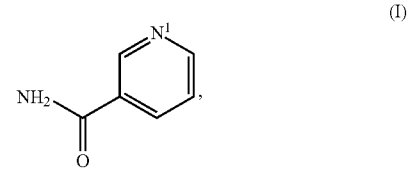

and a compound of formula (II):

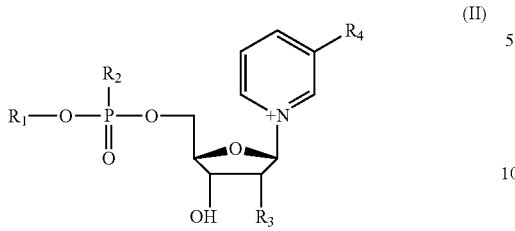

wherein the nicotinamide compound of formula (I) is provided with a nitrogen-bonded phosphoribose moiety at position 1 of the benzene ring, and wherein
$X^-$ is an anion,
$R_1$=H, $C_3H_7$, $C_4H_9$, $C_6H_{13}$, $C_{12}H_{25}$, NAD, $CH_2$-phenyl or $CH_2$—$CH_2$-phenyl group,
$R_2$=S, OH or NAD,
$R_3$=F, CN, Br, CI, and/or
$R_4$=$CONH_2$, COOH, COCN, or COF,
or a functional derivative thereof.

In a preferred embodiment of the invention, the compound of formula (II) does not have a substituent NAD, in particular neither $R_1$ nor $R_2$ are NAD.

A preferred CD38 antagonist compound is a compound of formula (II):

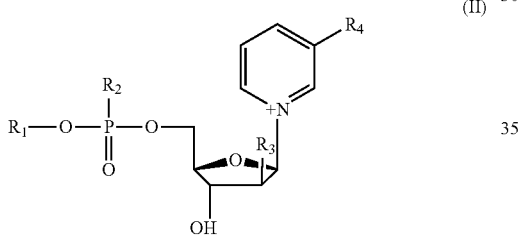

wherein the nicotinamide compound of formula (I) is provided with a nitrogen bonded phosphoribose moiety at position 1 of the benzene ring, and wherein:
$X^-$ is an anion,
$R_1$=H, $C_3H_7$, $C_4H_9$, $O_6H_{13}$, $C_{12}H_{25}$, $CH_2$-phenyl group or $CH_2$—$CH_2$-phenyl group,
$R_2$=S, OH, NAADP or 8-Bromo-NAD,
R3=F, CN, Br, CI, and/or
R4=$CONH_2$, COOH, COCN, or COF,
or a functional derivative thereof.

Nicotinamide is advantageously used as a CD38 antagonist in the subject to be treated at a concentration of at least 10 mmolar for the applications described in the context of the present invention.

In a particular embodiment, the CD38 antagonist is selected from CZ-17 wherein $R_1$=H, $R_2$=O, $R_3$=F and $R_4$=$CONH_2$; CZ-27 [2'-deoxy-2'-fluoro-β-nicotinamide arabinofuranoside-5'-(n-butyl) phosphate)] wherein $R_1$=$C_4H_9$, $R_2$=OH, $R_3$=F and $R_4$=$CONH_2$; CZ-57 wherein $R_1$=$O_3H_7$, $R_2$=OH, $R_3$=F and $R_4$=$CONH_2$; CZ-45 wherein $R_1$=$C_6H_{13}$, $R_2$=OH, $R_3$=F and $R_4$=$CONH_2$; CZ-48 wherein $R_1$=H, $R_2$=S, $R_3$=F and $R_4$=$CONH_2$ and CZ-53 wherein $R_1$=$C_{12}H_{25}$, $R_2$=OH, $R_3$=F and Ra=$CONH_2$.

In a particular preferred embodiment, the CD38 antagonist is selected from CZ-27, CZ-48, and a functional derivative thereof. A particularly preferred antagonist of CD38 is CZ-27.

Another particular compound according to the invention is an antagonist compound of cADPR, preferably a compound of formula (III):

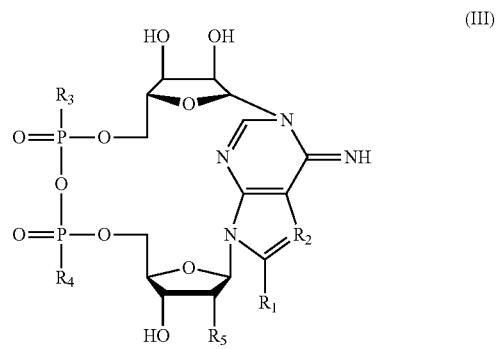

in which:
$R_1$=H, Br or $NH_2$,
$R_2$=N or C,
$R_3$=OH, F, CN or a group $CH_3COOCH_2O$,
$R_4$=OH, F, CN or a group $CH_3COOCH_2O$, and/or
$R_5$=OH, F or $H_2PO_3$,
or a functional derivative thereof.

In a particular preferred embodiment, the cADPR antagonist is 8-Bromo-cADPR ($C_{15}H_{20}BrN_5O_{13}P_2$ or 8-bromo adenosine diphosphate cyclic ribose), wherein $R_1$=Br, $R_2$=N, $R_3$=OH, $R_4$=OH and $R_5$=OH) or a functional derivative thereof. The 7-deaza-8-bromo-cADPR [wherein $R_1$=Br, $R_2$=O, $R_3$=OH, $R_4$=OH, and $R_5$=OH] and the 8-amino-adenosinediphosphate cyclic ribose [wherein $R_1$=$NH_2$, $R_2$=N, $R_3$=OH, $R_4$=OH, and $R_5$=OH] are examples of functional derivatives of 8-Bromo-cADPR.

Another particular compound according to the invention is an antagonist compound of NAADP, for example NAADP itself:

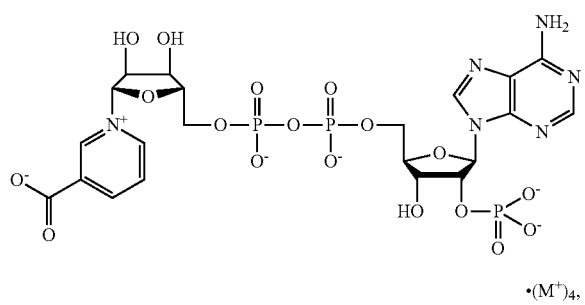

where $M^+$ is a cation.

NAADP is advantageously used with the subject to be treated at a concentration of at least 100 μmolar for the applications described in the context of the present invention.

Another NAADP antagonist compound is a compound of formula (IV):

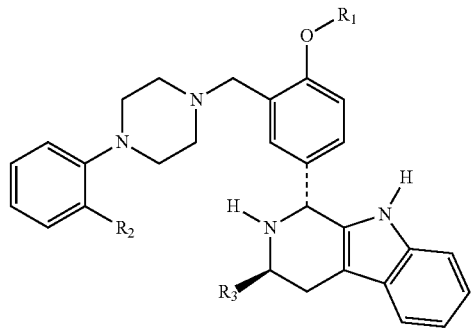

in which:
R$_1$=CH$_3$ or CN
R$_2$=F, CN, Br, and/or
R$_3$=COOR$_4$ where R$_4$=H or CH$_3$, or a functional derivative of the compound of formula (IV).

In a particular preferred embodiment, the antagonist of NAADP is NED-19 [C$_{30}$H$_{31}$FN$_4$O$_3$ or trans-NED 19 or (1R, 3S)-1-[3-[[4-(2-fluorophenyl)piperazin-1-yl]methyl]-4-methoxyphenyl]-2,3,4,9-tetrahydro-1H-pyrido[3,4-b]indole-3-carboxylic acid,] wherein R$_1$=CH$_3$, R$_2$=F and R$_3$=COOH, or functional derivative thereof.

In another particular embodiment, the NAADP antagonist is chosen from NED-K in which R$_1$=CH$_3$, R$_2$=CN and R$_3$=COOH, the NED-19.4 in which R$_1$=CH$_3$, R$_2$=F and R$_3$=COOCH$_3$, and a functional derivative thereof.

NED-K and NED-19.4 are examples of functional derivatives of NED-19.

For the purpose of the present invention, the term "functional derivative" is intended to mean a compound capable of: i) reducing or inhibiting the activity of calcium channels, and reducing the functional impairments of skeletal, smooth and/or cardiac muscle cells; ii) decreasing muscle necrosis possibly present in skeletal, smooth and/or cardiac muscle cells, and preferably, iii) reducing muscle inflammation.

The functional derivative is preferably capable of improving the skeletal muscle, cardiac muscle and diaphragm structure, as well as the skeletal muscle function of an "mdx mouse" as described in the experimental part of the present patent application. The improvement of the structure of the muscles and the diaphragm is validated by a decrease in cell necrosis demonstrated by histological staining (see Vianello et al., 2014, Neurobiol Dis., 71: 325-333). for example collagen, in the tissues of "mdx mice" treated. The improvement of skeletal muscle function may be measured with a Newton meter to determine the gripping force of the treated "mdx mouse" (see Vianello et al., 2014, FASEB J; 6): 2603-2619). The improvement of skeletal muscle fatigue resistance may be measured by the grid test (timing of the holding time of a mouse on an inverted grid, Vianello et al., 2014, FASEB J; 28 (6): 2603-2619).

As it is well established that muscle necrosis is due to an excessive increase of muscular calcium, the effectiveness of the functional derivative has to go through an improvement of the parameters of calcium homeostasis, as analyzed, for example, by confocal microscopy (cf Sarma et al., 2010, Proc. Natl. Acad. Sci. USA 107, 13165-13170, Vianello et al., 2014, FASEB J, 28 (6): 2603-2619), in mouse cardiomyocytes and DMD patient myotubes:

in the cardiomyocyte of "mdx mice", it has been shown that the calcium reserves of the sarcoplasmic reticulum are reduced, probably due to Ca$^{2+}$ leakage via RyRs which are abnormally sensitized. In addition, an increase in spontaneous spike/or wave calcium activity was observed in these cells. By way of example, the functional derivative must regulate the spontaneous calcium activity of cardiomyocytes of "mdx mice" by reversing at least one, preferably several, deleterious parameters in the "mdx mouse" (spontaneous calcium spikes and waves, sensitization of RyRs, etc.). The functional derivative is intended to reduce the number of cardiomyocytes exhibiting spontaneous calcium activity as well as the frequency of spontaneous calcium waves. Ideally, no spontaneous calcium activity of cardiomyocytes should be observed. If such activity may nevertheless be measured, then the frequency of spontaneous calcium waves must be significantly reduced.

culture myotubes, prepared from skeletal muscle of human DMD patients, exhibit significant spontaneous calcium activity in the form of calcium waves. By way of example, after preincubation with the functional derivative, the amplitude of the calcium waves must be significantly reduced. In addition, the number of myotubes with spontaneous calcium activity is reduced in a dose-dependent manner for de-concentration about 1 to 300 µM.

A particular object relates to a compound of the invention for use in preventing or treating DMD or BMD.

A particularly preferred compound of the invention is NED-19, which the inventors have demonstrated is particularly effective in preventing spontaneous calcium activity in human cardiomyocytes and myotubes of a patient with muscular dystrophy, particularly DMD. Another particularly preferred compound according to the invention is CZ-27, which the inventors have demonstrated to be effective in reducing the amplitude of spontaneous calcium waves in human myotubes of DMD patients.

Yet another particularly preferred compound according to the invention is 8-Bromo-cADPR, the inventors of which have been shown to be effective in reducing the amplitude of spontaneous calcium waves in human DMD patient myotubes.

In a preferred embodiment, NED-19 and 8-bromo-cADPR, or a combination of functional derivatives thereof, are used to prevent or treat myopathy or to treat muscular trauma in a subject.

The molecules identified by the inventors, and their functional derivatives, have in common, in particular, the reduction of the deleterious calcium activity and inflammation observed in myopathies, in particular in muscular dystrophies such as DMD and BMD. As explained in the experimental part, the inventors have demonstrated, in particular, the obtaining, with the aid of the molecules, of an improvement in the parameters of the calcium homeostasis of DMD.

A considerable advantage that the molecules (or compounds) of the invention selected by the inventors have over molecules used in the prior art is that, unlike the latter, they are able to fight very significantly against muscular necrosis. whatever the nature of the muscle concerned (skeletal, cardiac and/or smooth) and may be used preventively prior to any symptom, especially in subjects with a predisposition to the development of myopathy. In addition, they are not associated with any of the side effects listed for existing treatments, such as weight gain and fractures.

The subject concerned is an animal, typically a mammal, for example a mammal chosen from among a human being, a mouse, a rat, a pig or a dog. The subject concerned is preferably a human being of any kind. The human being is typically a male human in the case of X-related myopathies. As the mutation is recessive, a man carrying the mutant allele will be ill as he is hemizygote for the X chromosome. The presence of both mutant alleles is, however, necessary for the disease to be expressed in a female.

In the context of the present description, the dystrophies whose prevention or treatment is sought are direct attacks on one of the constituents of the muscular tissue. They result in a degeneration of muscle density. Typical examples of myopathies are muscular dystrophies and cardiomyopathies. Some myopathies are of genetic origin (X-linked, inherited or recessive), others are acquired.

X-linked myopathies include, for example, Duchenne muscular dystrophy (DMD), Becker muscular dystrophy (BMD), Emery-Dreyfus muscular dystrophy, vacuolar myopathy with autophagic glycogenosis (or myopathy with excessive authophagia).

Mainly inherited myopathies include muscular dystrophies of type 1A, 1B, 1C, 1D and 1E limb girdles, Steinert myotonic dystrophy, fascio-scapculo-humeral muscular dystrophy type 1A and 1B, oculopharyngeal muscular dystrophy, distal oculopharyngo myopathy, autosomal dominant Emery-Dreyfus muscular dystrophy, Bethlehem myopathy, desmin overload myopathy, tibial muscular dystrophy (or Udd distal myopathy), Welander distal myopathy, Laing distal myopathy, distal myopathy with weakness of the vocal cords and pharynx, congenital fibrosis of the extrinsic oculomotor muscles, inclusion body myopathy and muscular hypertrophy related to myostatin disorder.

Recessive-transmitted myopathies include muscular dystrophies of type 2A, 2B, 2C, 2D, 2E, 2F, 2G, 2H and 2I limb girdles, Nonaka distal myopathy (or distal myopathy with rimmed vacuoles), Miyoshi-type distal myopathy, autosomal recessive oculopharyngeal muscular dystrophy, inclusion body myopathy 2, autosomal recessive muscular dystrophy associated with epidermal bullosa, congenital muscular dystrophy due to merosine deficiency, congenital muscular dystrophy due to integrin deficiency, congenital muscular dystrophy with rigid spine, Muscle-Eye-Brain syndrome, Walker-Warburg syndrome and Emery-Dreyfuss type 3 muscular dystrophy.

Congenital myopathies with structural anomalies and acquired inflammatory myopathies are also included in the definition of "myopathies" as used in this text.

A compound or mixture of compounds according to the invention is advantageously used to prevent or treat at least one symptom of muscular dystrophy, preferably at least two or three symptoms, wherein the symptoms are selected according to muscle degeneration, muscle weakness (hypotonicity), myotonia, muscular heart failure, muscular respiratory failure, inflammation and mental retardation; to prevent or treat at least one symptom of cardiomyopathy, preferably at least two or three symptoms, wherein the symptoms are selected by arrhythmia, tachycardia, asthenia and dyspnoea; or to prevent or treat at least one symptom of muscular trauma, preferably at least two or three symptoms, wherein the symptoms are selected from contusion, curvature and contracture.

Examples of preferred compounds of interest, usable in the context of the invention for preventing or treating myopathy, in particular DMD or BMD, or muscular trauma, are identified below:

NED-19 [$C_{30}H_{31}FN_4O_3$ or trans-NED 19 or (1R, 3S)-1-[3-[[4-(2-fluorophenyl)piperazin-1-yl]methyl]-4-methoxyphenyl]-2,3, 4,9-tetrahydro-1H-pyrido[3,4-b] indole-3-carboxylicacid] with the formula below:

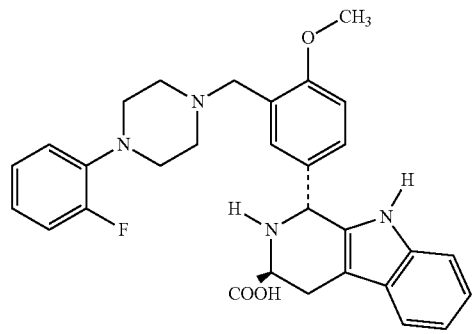

8-Bromo-cADPR (cyclic $C_{15}H_{20}BrN_5O_{13}P_2$ or 8-Bromo adenosine diphosphate ribose), having the formula below:

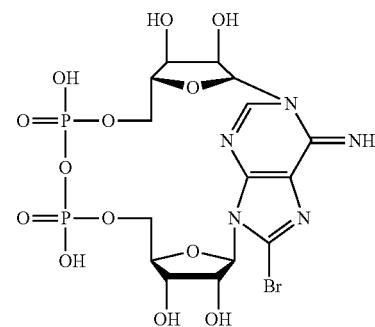 [SMILES: N=c1c2nc(Br)n3c2ncn1[C@H]1O[C@H](COP(=O)(O)OP(=O)(O)OC[C@H]2O[C@@H]3[C@@H](O)C2O)C(O)C1O]

CZ-27 [2'-Deoxy-2'-fluoro-β-nicotinamide arabinoribofuranoside-5'-(n-butyl) phosphate], having the formula below:

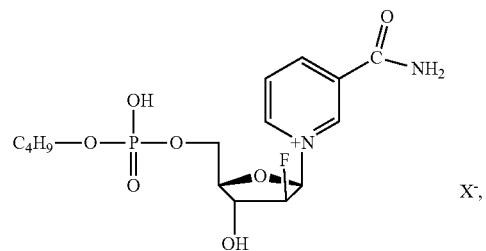

where X⁻ is an anion.

Preferred functional derivatives of compounds of interest which may be used in the context of the invention to prevent or treat muscular myopathy or trauma are chosen, for example, from NED-K, NED-19.4, CZ-17, CZ-45, CZ-48, CZ-53, CZ-57, 7-deaza-8-Bromo-cADPR and cyclic 8-amino-adenosine diphosphate ribose, preferably NED-K, NED-19.4, 7-deaza-8-Bromo-cADPR and 8-amino-adenosine diphosphate cyclic ribose. These derivatives have the same functional properties, listed above in the text, as the compounds of interest from which they derive.

Another object of the invention relates to a method for screening molecules or compounds of interest for preventing or treating myopathy or for treating muscular trauma. This method includes a step of evaluating the ability of test compounds to i) reduce or inhibit the calcium channel activity of skeletal, smooth and/or cardiac muscle cells, ii) reduce muscle necrosis of skeletal, smooth and/or cardiac muscle cells, and, preferably, iii) to reduce muscle inflammation. The method may be implemented in the presence of one or more of the compounds of interest according to the invention in order to test the ability of the test compounds to amplify the action of the compounds of interest or to act in synergy with them. Such methods may be implemented in an automated manner. Examples of such methods are described in U.S. Pat. No. 5,429,921. Pharmacological test compounds may come from chemical or natural compound libraries. Typically, several tests involving different concentrations of test compounds may be carried out in parallel in order to evaluate the responses obtained at the different concentrations; one of the concentrations, typically the absence of test compound (zero concentration) or a lower test compound concentration at the limit of detection, serving as a negative control. Reagents adapted to the implementation of such methods are known to those skilled in the art.

In a preferred embodiment of the invention, the compounds of interest are used to prevent and/or treat a pathology selected from muscular trauma, myopathy, in particular muscular dystrophy or cardiomyopathy, and/or a characteristic symptom or anomaly of such myopathy, preferably to prevent or treat DMD or BMD.

In a preferred embodiment of the invention, the compounds of interest are used to prevent and/or treat at least one symptom of myopathies, preferably at least two or three symptoms, wherein the symptoms are selected from among muscle degeneration, muscle weakness (hypotonicity), myotonia, heart failure of muscular origin, respiratory insufficiency of muscular origin, inflammation and mental retardation, preferably muscle degeneration, myotonia, cardiac insufficiency of muscular origin, respiratory insufficiency of muscular origin, and inflammation.

As previously explained, the current therapeutic approaches to myopathies involving corticosteroids only delay walking for 3 years, lead to weight gain that may compromise mobility, cause a reduction in bone mineral density with the increased risk of fractures, the occurrence of a cataract, as well as an increase in intraocular pressure. In contrast, β-blockers, phosphodiesterase inhibitors and angiotensin-converting enzyme inhibitors have no effect on cardiac or skeletal muscle degeneration. Moreover, they are generally used late in life for curative purposes in order to reduce the symptoms that appear, but can not be used preventively. In particular, there is currently no molecule or compound for treating, ideally preventing, necrosis affecting skeletal, smooth and heart muscles in an overall manner.

In a preferred embodiment of the invention, at least one compound of interest as described herein is used to prevent and/or treat muscular dystrophy, such as DMD or BMD, or to prevent and/or or treat cardiomyopathy, or to treat muscular trauma. NED-19, 8-Bromo-cADPR and CZ-27 are examples of compounds of interest used in a preferred manner for preventing and/or treating these pathologies. It should be noted that the functional derivatives of these compounds are themselves preferred compounds within the meaning of the invention. Mixtures of compounds of interest as described herein, or their functional derivatives, may also be used, such as a Ned-19/8-Bromo-cADPR, NED-19/CZ-27, 8-Bromo-cADPR/CZ-27 or NED-19/8-Bromo-cADPR/CZ-27 mixture.

In a particular embodiment of the invention, this at least one compound of interest, or this mixture of compounds of interest, may be used in combination with a distinct compound known to those skilled in the art and conventionally used:
in the treatment of muscular dystrophies, wherein the distinct compound is preferably selected from a glucocorticoid such as prednisolone and deflazacort, a beta-blocker such as albuterol, diphenylhydantoin (Dilantin®), mexiletine (Mexitil®), Baclofen (Lioresal), dantrolene (Dantrium®), carbamazepine (Tégrétol®), and an angiotensin converting enzyme (ACE) inhibitor;
in the treatment of cardiomyopathies, wherein the distinct compound is preferably selected from among acebutolol (Sectral®), albuterol, diphenylhydantoin (Dilantin®), mexiletine (Mexitil®), baclofen (Lioresal®), dantrolene (Dantrium®), carbamazepine (Tegretol®);
or in the treatment of muscular trauma, wherein the distinct compound is preferably selected from a venous or anti-oedematous tonic and an anti-inflammatory.

The veinotonic may be selected from among an hydrocyanoside, a nitroflavonoid and a flavonoid, for example from Adenyl®, Ampecyclal®, horse chestnut Arkogelules®, Bioveinal Elixir®, Cyclo3®, Climaxol®, Daflon®, Difrarel®, Diovenor®, Doxium®, Esbériven®, Flavan®, Flebosmil®, Ginkor®, Hirucrème®, Intercyton®, Madécassol®, Mediveine®, Phlebogel®, Phytomélis®, Relvène®, Rheoflux®, Thlascose®, Veinamitol®, Veinobiase®, Veliten®, Vivène®, Phlebosedol® herbal tea, Santane V3®, and Fluon®.

The anti-inflammatory drug is typically based on diclofenac or ibuprofen, wherein these treatments make it possible to observe satisfactory results in the management of pain, redness and heat following the contusion. The anti-inflammatory agent may be selected for example from AdvilGel 5%®, suractive Alesal®, Arnica complex No. 1®, Arnicagel®, and Arnicalme®.

Another object of the invention relates moreover to a composition in the form of a pharmaceutical composition comprising at least one compound of interest according to the invention, or mixture of compounds of interest according to the invention, and a pharmaceutically acceptable carrier (identified in this text as a "composition of interest"). A particular object relates typically to a pharmaceutical composition comprising, in addition to the at least one compound of interest according to the invention, or the mixture of compounds of interest according to the invention, at least one other compound (different from the compounds of interest used in the context of the invention for preventing or treating a therapeutically active myopathy (and recognized as such by those skilled in the art), such as an immunological adjuvant or a compound active in prevention or treatment, typically the treatment of a characteristic symptom or anomaly of myopathy (as described in this text for example).

The invention also relates to a composition as described herein for use in treating muscular trauma or for preventing or treating myopathy, typically a pathology selected from muscular dystrophy, or a characteristic symptom or anomaly of the muscular dystrophy, and cardiomyopathy, preferably to prevent or treat DMD or BMD.

The term "treatment" refers to curative, symptomatic or preventive treatment. The compounds of the present invention may thus be used in subjects (such as mammals, in particular humans) with a declared disease. The compounds of the present invention may also be used to delay or slow progression or prevent further progression of the disease, thereby improving the condition of the subjects. The compounds of the present invention may finally be administered for "prevention" in the case of non-diseased subjects, but who may develop the disease normally, or who present a significant risk of developing the disease, such as predisposed subjects, especially genetically predisposed subjects.

The compound(s) of interest or compositions according to the invention may be administered in different ways and in different forms.

Thus, in a typical embodiment, the compound(s) of interest are administered to the subject, together or separately, and the compound(s) of interest or compositions according to the invention are administered continuously or sequentially, once or several times a day (daily administration), once or several times a week (weekly administration), or once or several times a month (monthly administration), throughout the duration of the treatment, i.e. until the improvement of the symptoms of the pathology treated, preferably the disappearance of all or part of the symptoms.

If necessary, the daily dose may, for example, be administered in two, three, four, five, six or more doses taken daily or in multiple sub-doses administered at appropriate intervals during the day.

These compounds or compositions may, for example, be administered systemically, orally, parenterally, by inhalation or by injection, for example intravenously, intraperitoneally, intramuscularly, subcutaneously, trans-dermally, intravenously or intra-arterial, etc. As a long-term treatment, the preferred route of administration will be sublingual, oral, intramuscular, or transcutaneous.

The compositions may be formulated as injectable suspensions, oils, suppositories, capsules, aerosols, etc., optionally using dosage forms or devices providing sustained and/or delayed release. For the injections, the compounds are generally packaged in the form of liquid suspensions, which may be injected by means of syringes or infusions, for example.

It is to be understood that the flow rate and/or the dose injected may be adapted by those skilled in the art depending on the patient, the pathology, the mode of administration, etc. In general, the daily dose of the compound will be the minimum dose to achieve the therapeutic effect.

The amount of compound present in the therapeutic composition may be modulated in order to obtain a circulating level of active ingredient necessary to obtain the desired therapeutic effect for a particular patient, composition, mode of administration, and preferably without toxicity to the patient. The amount selected will depend on multiple factors, in particular the mode of administration, the duration of administration, the timing of administration, the rate of elimination of the compound, the various products used in combination with the compound, age, weight and physical condition of the patient, as well as its medical history, and other information known in medicine.

Typically, the compounds are administered to the subject to be treated with doses ranging between 10 mg and 1 g per kg, preferably between 20 mg and 0.5 g per kg. On the other hand, the compositions according to the invention may comprise in addition, other agents or active ingredients as explained above. The compositions according to the invention may also comprise one or more excipients or vehicles, which are pharmaceutically acceptable. For example, saline, physiological, isotonic, buffered solutions etc. that are compatible with a pharmaceutical use and known to those skilled in the art, may be mentioned. The compositions may contain one or more agents or vehicles selected from among dispersants, solubilizers, stabilizers, preservatives, etc.

The invention also relates to methods for preventing or treating a myopathy in a subject, typically a muscular dystrophy or a cardiomyopathy, comprising the administration to a subject suffering from a myopathy or likely to develop a myopathy, of a compound or composition of interest as described herein to prevent or treat the myopathy.

It also relates to the methods for preventing or treating a subject suffering from myopathy as described herein, typically a muscular dystrophy or a cardiomyopathy, or a subject suffering from a muscular trauma. These methods all comprise a step of administration to a subject suffering from such a pathology or capable of developing such a pathology, of a compound or composition of interest as described herein to prevent or treat the pathology.

Finally, the invention relates to a prophylactic or therapeutic kit comprising a compound or a composition according to the invention and at least one additional compound such as an immunological adjuvant or a prophylactically or therapeutically active compound (recognized as such by those skilled in the art, and different from compounds according to the invention), in particular a compound active in the treatment of muscular trauma, heart disease, or muscular dystrophies, typically at least one characteristic symptom or anomaly of DMD and/or BMD, wherein the compounds are preferably in separate containers, preferably sterile.

In a particular kit, the compound according to the invention is a compound selected from an antagonist of ADP ribosylcyclase, typically CD38, a cADPR antagonist, and/or an antagonist of NAADP, and a mixture thereof, wherein a compound is preferably selected from among NED-19, 8-Bromo-cADPR, CZ-27, a functional derivative of one of the compounds, and a mixture thereof.

In a particular kit, the at least one distinct therapeutically active compound, in particular for the treatment of muscular dystrophies, is selected from a glucocorticoid such as prednisolone or deflazacort, a betablocker such as albuterol, diphenylhydantoin (Dilantin®), mexiletine (Mexitil®), baclofen (Lioresal), dantrolene (Dantrium®) or carbamazepine (Tégrétol®), an angiotensin converting enzyme (ACE) inhibitor and a nucleotide to modify the expression of dystrophin, typically to restore the physiological (vs pathological) expression of dystrophin [such a sequence may be in the form of an antisense oligonucleotide, a morpholino, a tricyclic oligomer DNA ("tcDNA"), a vector, for example an AAV vector carrying a U7 transgene, etc.].

The kit may further include an instruction leaflet including information regarding the administration of an effective amount of each compound for a given subject to prevent or treat myopathy in that subject.

The following figures and examples illustrate the invention without limiting its scope.

EXAMPLES

Generation of mdx/CD38$^{-/-}$ mouse:

CD38 deficient mice and mdx mice are used. These mice were crossed to obtain double mutants (F2 generation, FIG. 2). Five mouse genotypes are thus obtained: the control mice are C57BL/10 and C57BL/6; the mutated mice are the mdx, from the C57BL/10 strain, and the CD38$^{-/-}$ from the C57BL16 strain; and finally mdx/CD38$^{-/-}$ mice derived from the cross between female mdx mice and male CD38$^{-/-}$ mice. Their corresponding control is noted WT/CD38$^{-/-}$ (see FIG. 2). From the generated mice, only male mice were used in the experiments.

Evaluation of Muscle Structure and Function in Mice:

A phenotypic evaluation of the double mutant was performed. For this, animals aged 4 to 12 months were used. In mdx mice, cardiac necrosis develops from 4 months and evolves little until 15 months when it becomes more significant whereas the necrosis of the diaphragm is already very advanced from the age of 4 months. In the case of the mdx/CD38$^{-/-}$ mice, a very significant reduction of the necrosis of the diaphragm (see FIG. 3B) and also a reduction of the cardiac necrosis (see FIG. 3A) associated with a functional improvement of the skeletal muscles (see FIG. 3C, 3D) and the diaphragm (see FIG. 3E, 3F) have been observed.

Evaluation of the Spontaneous Calcium Activity of Mouse Cardiomyocytes:

In the mdx cardiomyocyte, it was shown that the calcium reserves of the sarcoplasmic reticulum were reduced, probably due to $Ca^{2+}$ leakage through RyRs that are abnormally sensitized. In addition, an increase in spike-like spontaneous calcium activity was observed in mdx.

In order to study the impact of the absence of CD38 on these parameters, the different parameters of spontaneous spike activity and calcium waves were studied. An increase in spontaneous calcium activity (spontaneous spikes and calcium waves) associated with increased susceptibility of RyRs was observed in the cardiomyocyte of mdx mice aged 4-5 months (see FIG. 4A). The increased frequency of these spontaneous calcium events may lead to arrhythmias (when they spread to the whole heart tissue) as well as to a long-term cardiac hypertrophy associated with a change in the $Ca^{2+}$-dependent gene expression.

The protective effect of the CD38 deletion in mice was then observed by comparing cardiomyocytes of the double-mutant model with cardiomyocytes of mdx mice. The spontaneous calcium activity of mdx/CD38$^{-/-}$ cardiomyocytes is very small compared to mdx (spikes and calcium waves, see FIG. 4A). The results show a reduction in the sensitivity of RyRs in mdx/CD38$^{-/-}$ mice (not shown). CD38 deletion in mdx/CD38$^{-/-}$ favor its protective role in DMD, with the reversal of many deleterious parameters in mdx mice (spontaneous calcium spikes and waves, sensitization of RyRs). Application of CD38 antagonist CZ-27 (see FIG. 7A) to mdx mouse cardiomyocytes also enhances some parameters such as a reduction in spikes frequency (see FIG. 4B). When mdx mouse cardiomyocytes are incubated in the presence of NAADP antagonist NED-19 (see FIG. 6), there is a significant reduction in the number of cardiomyocytes exhibiting spontaneous calcium activity (not shown). In the rare cases of spontaneous activity in the presence of NED-19, the frequency of spontaneous calcium waves is greatly reduced (see FIG. 4C).

Effect of NED-19 on Spontaneous Calcium Activity in the Myotube of Patients with DMD (See FIG. 5):

In parallel with mouse cardiomyocyte studies, two lines of human skeletal myotubes (a patient cell line with DMD and a control line) were used. Human myotubes are particularly suitable for evaluating a pharmacological tool from a therapy perspective. The inventors first tested the CZ-27, the NED-19 antagonist of NAADP (the most efficient messenger produced by CD38), and 8-bromo-cADP-ribose (a cADP-ribose antagonist produced by CD38. The cells were loaded with Fluo-4 AM and recorded by confocal microscopy.

Only 13% of the myotubes from the healthy control line showed spontaneous calcium activity (calcium waves), whereas about 50% of the myotubes from the DMD patient line showed spontaneous calcium activity (see FIG. 5A, B). The amplitude of the calcium waves was reduced by 40% (see FIG. 5A) compared to that of the untreated DMD myotubes. When the cultures of DMD myotubes were preincubated with CZ-27 (10, 50 and 100 µM), the inventors found that the amplitude of the calcium waves was reduced in a dose-dependent manner by up to 80% compared with that of the untreated DMD myotubes (see FIG. 5C). A 40% reduction in the amplitude of the calcium waves is also observed when the cells are treated with 100 µM of 8-Bromo-cADPR or NED-19 (see FIG. 5C). When cultures of DMD myotubes were preincubated with NED-19, the number of myotubes with spontaneous calcium activity was reduced in a dose-dependent manner for concentrations of 2 to 300 µM (60% to 100 µM reduction) (see FIG. 5D). In addition, when cultures of DMD myotubes were preincubated with NAADP at 100 µM, the number of myotubes with spontaneous calcium activity was reduced (75% reduction with 100 µM NAADP) (see FIG. 8D).

The results obtained by the inventors show that NED-19 greatly reduces the occurrence and amplitude of spontaneous calcium waves suggesting that NAADP is a central element in the genesis of abnormal calcium signals in this DMD line. CZ-27 is it the most effective in reducing the amplitude of spontaneous calcium waves in human myotubes of DMD patients. 8-Bromo-cADPR has an effect on the amplitude of spontaneous calcium waves in human myotubes of DMD patients equivalent to NED-19 and may be used in synergy with it.

CONCLUSION

Inhibition of the CD38 pathway shows a significant benefit for necrotic involvement in the heart and diaphragm, and functional impairment of skeletal muscle. The results obtained on both the cardiomyocyte and the human myotube line, demonstrate that CD38 and its metabolites (including NAADP) are key therapeutic targets in the treatment of myopathies, DMD and BMD in particular, NED-19, 8-Bromo-cADPR, CZ-27 compounds and their derivatives are compounds that are directly usable in the prevention and treatment of the myopathies, wherein they are able to normalize the key parameters of muscle calcium homeostasis and to reduce the muscle necrosis in the mdx mouse and in a cell line derived from a patient with DMD.

REFERENCES

Allen, D. G., Gervasio, O. L., Yeung, E. W., and Whitehead, N. P. (2010). Calcium and the damage pathways in muscular dystrophy. Can. J. Physiol. Pharmacol. 88, 83-91.

Altamirano, F., López, J. R., Henríquez, C., Molinski, T., Allen, P. D., and Jaimovich, E. (2012). Increased resting intracellular calcium modulates NF-κB-dependent inducible nitric-oxide synthase gene expression in dystrophic mdx skeletal myotubes. J. Biol. Chem. 287, 20876-20887.

Au, C. G., Butler, T. L., Sherwood, M. C., Egan, J. R., North, K. N., and Winlaw, D. S. (2011). Increased connective tissue growth factor associated with cardiac fibrosis in the mdx mouse model of dystrophic cardiomyopathy. Int. J. Exp. Pathol. 92, 57-65.

Basset, O., Boittin, F.-X., Cognard, C., Constantin, B., and Ruegg, U. T. (2006). Bcl-2 overexpression prevents calcium overload and subsequent apoptosis in dystrophicmyotubes. Biochem. J. 395, 267-276.

Capel R A, Bolton E L, Lin W K, Aston D, Wang Y, Liu W, Wang X, Burton R B, Bloor-Young D, Shade K T, Ruas M, Parrington J, Churchill G C, Lei M, Galione A, Terrar D A. (2015) Two pore channels (TPC2s) and nicotinic acid adenine dinucleotide phosphate (NAADP) at lysosomal-sarcoplasmic reticular junctions contribute to acute and chronic β-adrenoceptor signaling in the heart. J Biol Chem. 2015 Oct. 5. pii: jbc.M115.684076. [Epub ahead of print]

Cosker, F., Cheviron, N., Yamasaki, M., Menteyne, A., Lund, F. E., Moutin, M.-J., Galione, A., and Cancela, J.-M. (2010). The ecto-enzyme CD38 is a nicotinic acid adenine dinucleotide phosphate (NAADP) synthase that couples receptor activation to Ca2+ mobilization from lysosomes in pancreatic acinar cells. J. Biol. Chem. 285, 38251-38259.

Davidson S M, Foote K, Kunuthur S, Gosain R, Tan N, Tyser R, Zhao Y J, Graeff R, Ganesan A, Duchen M R, Patel S, Yelton D M. (2015) Inhibition of NAADP signalling on reperfusion protects the heart by preventing lethal calcium oscillations via two-pore channel 1 and opening of the mitochondrial permeability transition pore. Cardiovasc Res. December 1; 108(3):357-66.

Galione, A. (2015). A primer of NAADP-mediated Ca(2+) signalling: From sea urchin eggs to mammalian cells. Cell Calcium. July; 58 (1):27-47.

Kwong, A. K. Y., Chen, Z., Zhang, H., Leung, F. P., Lam, C. M. C., Ting, K. Y., Zhang, L., Hao, Q., Zhang, L.-H., and Lee, H. C. (2012). Catalysis-based inhibitors of the calcium signaling function of CD38. Biochemistry (Mosc.) 51, 555-564.

Lewis, A. M., Aley, P. K., Roomi, A., Thomas, J. M., Masgrau, R., Garnham, C., Shipman, K., Paramore, C., Bloor-Young, D., Sanders, L. E. L., et al. (2012). β-Adrenergic receptor signaling increases NAADP and cADPR levels in the heart. Biochem. Biophys. Res. Commun. 427, 326-329.

Naylor, E., Arredouani, A., Vasudevan, S. R., Lewis, A. M., Parkesh. R., Mizote, A., Rosen, D., Thomas, J. M., Izumi, M., Ganesan, A., et al. (2009). Identification of a chemical probe for NAADP by virtual screening. Nat. Chem. Biol. 5, 220-226.

Nebel, M., Schwoerer, A. P., Warszta, D., Siebrands, C. C., Limbrock, A.-C., Swarbrick, J. M., Fliegert, R., Weber, K., Bruhn, S., Hohenegger, M., et al. (2013). Nicotinic acid adenine dinucleotide phosphate (NAADP)-mediated calcium signaling and arrhythmias in the heart evoked by β-adrenergic stimulation. J. Biol. Chem. 288, 16017-16030.

Partida-Sánchez, S., Cockayne, D. A., Monard, S., Jacobson, E. L., Oppenheimer, N., Garvy, B., Kusser, K., Goodrich, S., Howard, M., Harmsen, A., et al. (2001). Cyclic ADP-ribose production by CD38 regulates intracellular calcium release, extracellular calcium influx and chemotaxis in neutrophils and is required for bacterial clearance in vivo, Nat. Med. 7, 1209-1216.

Quinlan, J. G., Hahn, H. S., Wong, B. L., Lorenz, J. N., Wenisch, A. S., and Levin, L. S. (2004). Evolution of the mdx mouse cardiomyopathy: physiological and morphological findings. Neuromuscul Disord 14, 491-496.

Rosen et al., J Biol Chem (2009) 284, 34930-34934

Sabourin, J., Harisseh, R., Harnois, T., Magaud, C., Bourmeyster, N., Déliot, N., and Constantin, B. (2012). Dystrophin/α1-syntrophin scaffold regulated PLC/PKC-dependent store-operated calcium entry inmyotubes. Cell Calcium.

Sarma, S., Li, N., van Oort, R. J., Reynolds, C., Skapura, D. G., and Wehrens, X. H. T. (2010). Genetic inhibition of PKA phosphorylation of RyR2 prevents dystrophic cardiomyopathy. Proc. Natl. Acad. Sci. U.S.A. 107, 13165-13170.

Sethi et al., J Biol Chem. 1997. Vol. 272, No. 26, pp. 16358-16363

Spurney, C. F., Knoblach, S., Pistilli, E. E., Nagaraju, K., Martin, G. R., and Hoffman, E. P. (2008). Dystrophin-deficient cardiomyopathy in mouse: expression of Nox4 and Lox are associated with fibrosis and altered functional parameters in the heart. Neuromuscul. Disord. NMD 18, 371-381.

Takahashi, J., Kagaya, Y., Kato, 1., Ohta, J., Isoyama, S., Miura, M., Sugai, Y., Hirose, M., Wakayama, Y., Ninomiya, M., et al. (2003). Deficit of CD38/cyclic ADP-ribose is differentially compensated in hearts by gender. Biochem. Biophys. Res. Commun. 312, 434-440.

Vianello, S., Consolaro, F., Bich, C., Cancela, J.-M., Roulot, M., Lanchec, E., Touboul, D., Brunelle, A., Israël, M., Benoit, E., et al. (2014a). Low doses of arginine butyrate derivatives improve dystrophic phenotype and restore membrane integrity in DMD models. FASEB J. Off. Publ. Fed. Am. Soc. Exp. Biol.; 28(6):2603-2619.

Vianello, S., Bouyon, S., Benoit, E., Sebrié, C., Boerio, D., Herbin, M., Roulot, M., Fromes, Y., de la Porte, S. (2014). Arginine butyrate per os protects mdx mice against cardiomyopathy, kyphosis and changes in axonal excitability. Neurobiol Dis.; 71:325-333.

Walseth, T. F., and Lee, H. C. (1993). Synthesis and characterization of antagonists of cyclic-ADP-ribose-induced Ca2+ release. Biochim. Biophys. Acta 1178, 235-242.

Wang, S., Zhu, W., Wang, X., Li, J., Zhang, K., Zhang, L., Zhao, Y.-J., Lee, H. C., and Zhang, L. (2014). Design, synthesis and SAR studies of NAD analogues as potent inhibitors towards CD38NADase. Mol. Basel Switz. 19, 15754-15767.

Wei, W.-J., Sun, H.-Y., Ting, K. Y., Zhang, L.-H., Lee, H.-C., Li, G.-R., and Yue, J. (2012). Inhibition of cardiomyocytes differentiation of mouse embryonic stem cells by CD38/cADPR/Ca2+ signaling pathway. J. Biol. Chem. 287, 35599-35611.

The invention claimed is:

1. A method of treatment of a disorder selected from the group consisting of Duchenne muscular dystrophy (DMD), Becker muscular dystrophy (BMD), a cardiomyopathy and a muscular myopathy in a subject in need thereof, comprising administering to the subject a compound selected from the group consisting of an ADP ribosylcyclase antagonist compound selected from the group consisting of a nicotinamide of formula (I):

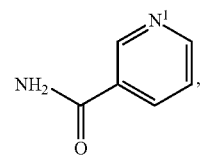

and
a compound of formula (II):

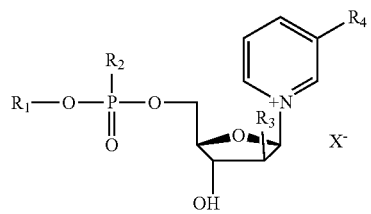
(II)

wherein the nicotinamide of formula (I) is provided with a nitrogen bonded phosphoribose moiety at position 1 of the pyridine ring, and
wherein in formula II:
X⁻ is an anion,
$R_1$=$C_4H_9$,
$R_2$=OH,
$R_3$=F, and
$R_4$=$CONH_2$;
a cyclic ADP ribose (cADPR) antagonist compound of formula (III):

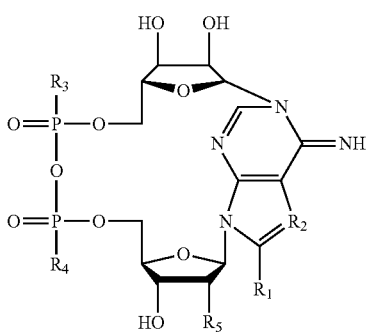
(III)

in which:
$R_1$=Br,
$R_2$=N,
$R_3$=OH,
$R_4$=OH, and
$R_5$=OH; and
an NAADP antagonist compound selected from the group consisting of NAADP itself of formula:

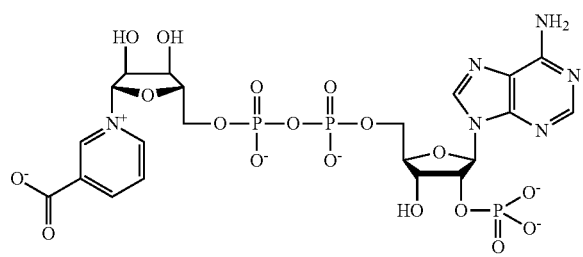
·(M⁺)₄, wherein M⁺ is a cation,
at a concentration of at least 100 µmolar, and
a compound of formula (IV):

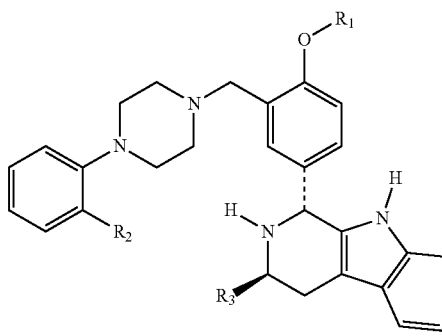
(IV)

in which:
$R_1$=$CH_3$,
$R_2$=F, and
$R_3$=$COOR_4$ where $R_4$=H.

2. The method according to claim 1, wherein the CD38 antagonist compound is the compound CZ-27, which is 2'-Deoxy-2'-fluoro-β-nicotinamide arabinofuranoside-5'-(n-butyl) phosphate], having the formula below:

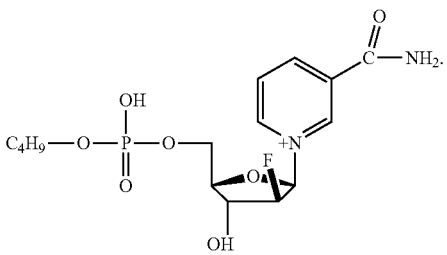

3. The method according to claim 1, wherein the cADPR antagonist compound is 8-Bromo-cADPR ($C_{15}H_{20}BrN_5O_{13}P_2$).

4. The method according to claim 1, wherein the NAADP antagonist compound is NED-19 ($C_{30}H_{31}FN_4O_3$) in which $R_1$=$CH_3$, $R_2$=F and $R_3$=COOH.

5. The method according to claim 1, wherein the subject is in need of treatment of at least one symptom of DMD or BMB selected from the group consisting of muscle degeneration, muscle weakness (hypotonicity), myotonia, heart failure of muscular origin and muscular respiratory failure.

6. The method according to claim 1, wherein the subject is in need of treatment of DMD or BMD, further comprising administering a compound as defined in claim 1, in combination with a distinct compound for treatment of the dystrophy, wherein the distinct compound for the treatment of the dystrophy is a glucocorticoid selected from the group consisting of prednisolone and deflazacort, a beta-blocker selected from the group consisting of albuterol, diphenylhydantoin, mexiletine, baclofen, dantrolene and carbamazepine or an angiotensin converting enzyme (ACE) inhibitor.

7. The method according to claim 1, wherein the subject is in need of treatment for cardiomyopathy, further comprising administering a compound as defined in claim 1, in combination with a distinct compound for treatment of cardiomyopathies, wherein the distinct compound is selected from the group consisting of acebutolol, albuterol, diphenylhydantoin, mexiletine, Baclofen, dantrolene and carbamazepine.

8. The method according to claim 1, further comprising administering the compound as defined in claim 1 in combination with a distinct compound for treatment of a muscular myopathy, wherein the distinct compound is selected from the group consisting of a venous tonic compound, an anti-edematous compound and an anti-inflammatory compound, wherein the venous tonic compound and the anti-edematous compound are selected from the group consisting of a hydrocyanoside, a nitroflavonoid and a flavonoid; and wherein the anti-inflammatory compound is selected from the group consisting of diclofenac and ibuprofen based medicines.

9. The method according to claim 1, wherein the compound of formula (II) is formula (II) as defined in claim 1 and is the compound CZ-27 in which $R_1$=$C_4H_9$, $R_2$=OH, $R_3$=F and $R_4$=$CONH_2$.

10. The method according to claim 1, wherein the compound of formula (III) is 8-Bromo-cADPR ($C_{15}H_{20}BrN_5O_{13}P_2$).

11. The method according to claim 1, wherein compound of formula (IV) is NED-19 ($C_{30}H_{31}FN_4O_3$) in which $R_1$=$CH_3$, $R_2$=F and $R_3$=COOH.

12. A pharmaceutical composition comprising a compound selected from the group consisting of:
an ADP ribosylcyclase antagonist compound selected from the group consisting of nicotinamide of formula (I):

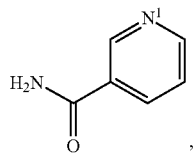

(I)

and compounds of formula (II):

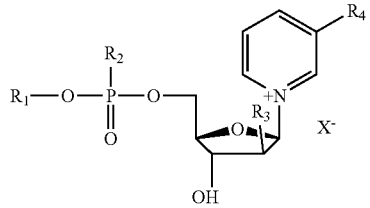

(II)

wherein the nicotinamide of formula (I) is provided with a nitrogen bonded phosphoribose moiety at position 1 of the pyridine ring, and
wherein in formula (II):
$X^-$ is an anion,
$R_1$=$C_4H_9$,
$R_2$=OH,
$R_3$=F, and
$R_4$=$CONH_2$;

a cADPR antagonist compound of formula (III):

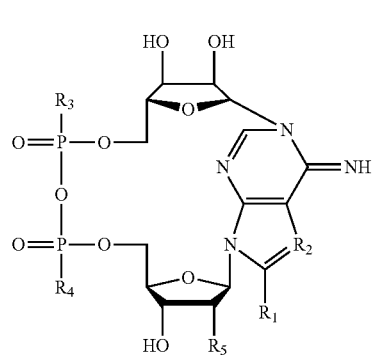

(III)

in which:
$R_1$=Br,
$R_2$=N,
$R_3$=OH,
$R_4$=OH, and
$R_5$=OH; and
an NAADP antagonist compound selected from the group consisting of: NAADP itself of formula:

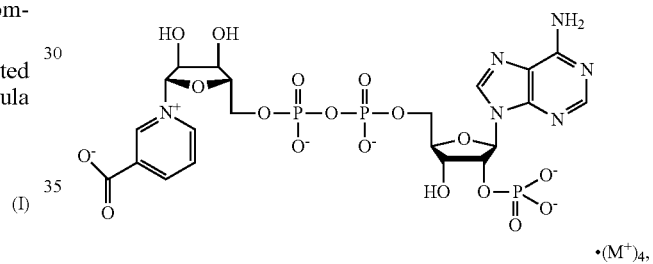

·$(M^+)_4$, where $M^+$ is a cation, and
a compound of formula (IV):

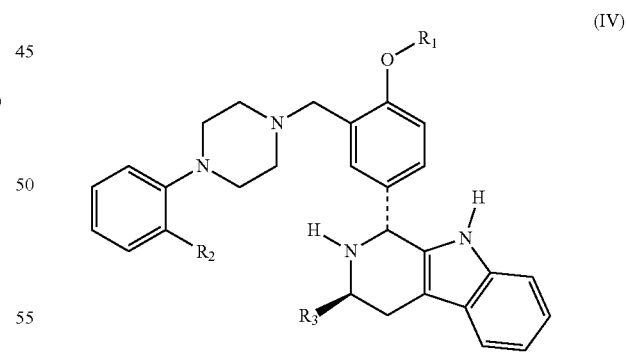

(IV)

in which:
$R_1$=$CH_3$,
$R_2$=F, and
$R_3$=$COOR_4$ where $R_4$=H;
and a pharmaceutically acceptable carrier.

13. A therapeutic kit comprising a compound selected from the group consisting of:
an ADP ribosylcyclase antagonist compound selected from the group consisting of nicotinamide of formula (I):

(I)

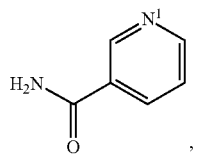

and compounds of formula (II):

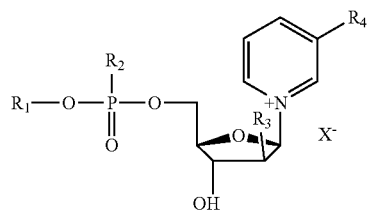
(II)

wherein the nicotinamide of formula (I) is provided with a nitrogen bonded phosphoribose moiety at position 1 of the pyridine ring, and
wherein in formula II:
X⁻ is an anion,
$R_1=C_4H_9$,
$R_2=OH$,
$R_3=F$, and
$R_4=CONH_2$;
a cADPR antagonist compound of formula (III):

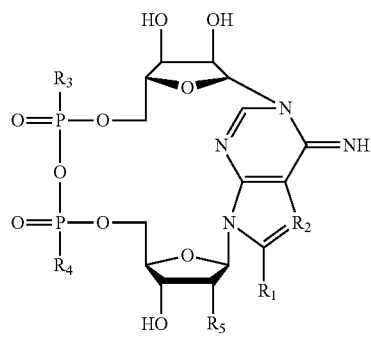
(III)

in which:
$R_1=Br$,
$R_2=N$,
$R_3=OH$,
$R_4=OH$, and
$R_5=OH$; and
an NAADP antagonist compound selected from the group consisting of: NAADP itself of formula:

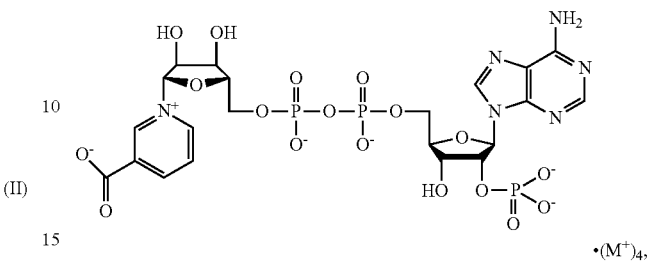

$\cdot(M^+)_4$, where AV is a cation, and
a compound of formula (IV):

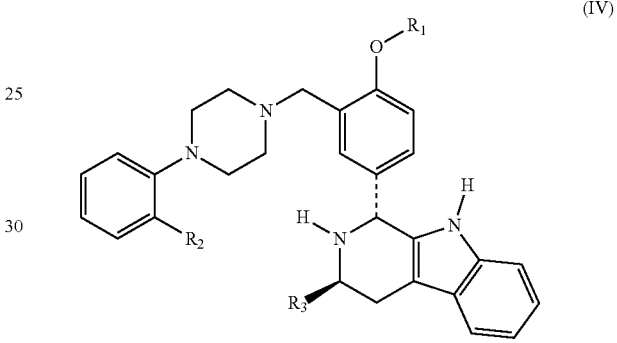
(IV)

in which:
$R_1=CH_3$,
$R_2=F$, and
$R_3=COOR_4$ where $R_4=H$
and at least one compound selected from the group consisting of a glucocorticoid selected from the group consisting of prednisolone and deflazacort; a beta-blocker selected from the group consisting of albuterol, diphenylhydantoin, mexiletine, baclofen, dantrolene and carbamazepine; an angiotensin converting enzyme (ACE) inhibitor; and a nucleic acid that specifically binds to and reduces the expression of pathological dystrophin, wherein the nucleic acid is selected from the group consisting of an antisense oligonucleotide, a morpholino oligomer and a tricyclic oligomer DNA (tcDNA).

14. The therapeutic kit according to claim 13, further comprising separately providing separate single samples of the listed compounds.

* * * * *